(12) United States Patent
Biederman et al.

(10) Patent No.: US 10,105,100 B2
(45) Date of Patent: Oct. 23, 2018

(54) DISPLAY ON A BANDAGE-TYPE MONITORING DEVICE

(71) Applicant: Verily Life Sciences LLC, Mountain View, CA (US)

(72) Inventors: William James Biederman, Fox Island, WA (US); Brian Otis, Saratoga, CA (US); Zenghe Liu, Alameda, CA (US); Jaclyn Leverett Wasson, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 469 days.

(21) Appl. No.: 14/810,588

(22) Filed: Jul. 28, 2015

(65) Prior Publication Data
US 2017/0027514 A1    Feb. 2, 2017

(51) Int. Cl.
*A61B 5/00* (2006.01)
*G06F 1/16* (2006.01)
(Continued)

(52) U.S. Cl.
CPC .......... *A61B 5/6832* (2013.01); *A61B 5/1451* (2013.01); *A61B 5/1473* (2013.01);
(Continued)

(58) Field of Classification Search
CPC .... A61B 5/1451; A61B 5/6832; A61B 5/6833
See application file for complete search history.

(56) References Cited

U.S. PATENT DOCUMENTS 7,652,188 B2   1/2010  Levanon et al.
7,949,382 B2   5/2011  Jina
(Continued)

FOREIGN PATENT DOCUMENTS

WO   2015017712   2/2015

OTHER PUBLICATIONS

Getting starting with Guardian Real-Time Continuous Glucose Monitoring, product guide, 2009, Medtronic, Northridge, CA.
(Continued)

*Primary Examiner* — Puya Agahi
(74) *Attorney, Agent, or Firm* — McDonnell Boehnen Hulbert & Berghoff LLP

(57) ABSTRACT

A body-mountable device includes a flexible substrate configured for mounting to a skin surface. The flexible substrate is configured to be adhered or otherwise mounted to the skin in a manner that minimally impacts activities of the body. The device includes a flexible display configured to provide indications to a user, e.g., indications of sensor readings, medical alerts, or operational states of the device. The display could be operated on a very low power budget, e.g., the display could be operated intermittently. In some examples, the display could include an e-paper display or similar low power display elements. In some examples, elements of the display, e.g., electrodes of a multi-segment display, could be formed on the flexible substrate such that additional elements of the display, e.g., a layer of display medium and a layer of transparent conductor, could be adhered or otherwise attached to the formed elements.

13 Claims, 7 Drawing Sheets

(51) Int. Cl.
*A61B 5/145* (2006.01)
*A61B 5/1473* (2006.01)

(52) U.S. Cl.
CPC ........ *A61B 5/14532* (2013.01); *A61B 5/6833* (2013.01); *A61B 5/7275* (2013.01); *A61B 5/742* (2013.01); *A61B 5/7475* (2013.01); *G06F 1/163* (2013.01); *G06F 1/1635* (2013.01); *G06F 1/1643* (2013.01); *G06F 1/1652* (2013.01); *G06F 1/1656* (2013.01); *A61B 2560/0412* (2013.01); *A61B 2560/0487* (2013.01)

(56) References Cited

U.S. PATENT DOCUMENTS

| | | |
|---|---|---|
| 8,202,697 B2 | 6/2012 | Holmes |
| 8,326,652 B2 | 12/2012 | Sweeney |
| 8,385,998 B2 | 2/2013 | Zhang et al. |
| 8,512,245 B2 | 8/2013 | Markle et al. |
| 8,956,289 B2 | 2/2015 | Kitajima et al. |
| 8,979,755 B2 | 3/2015 | Szydlo-Moore et al. |
| 2007/0123756 A1* | 5/2007 | Kitajima ............ A61B 5/14552 600/300 |
| 2010/0317951 A1* | 12/2010 | Rutkowski ......... A61B 5/14532 600/365 |
| 2012/0296187 A1 | 11/2012 | Henning et al. |
| 2013/0030259 A1* | 1/2013 | Thomsen ........... A61B 5/02028 600/301 |
| 2013/0041235 A1 | 2/2013 | Rogers et al. |
| 2014/0180137 A1 | 6/2014 | Stivoric et al. |
| 2014/0275899 A1 | 9/2014 | Gottlieb et al. |
| 2015/0005589 A1 | 1/2015 | Bly et al. |
| 2015/0018639 A1 | 1/2015 | Stafford |
| 2015/0182128 A1* | 7/2015 | Magi .................... A61B 5/0205 340/539.12 |
| 2016/0029977 A1* | 2/2016 | Di Resta ............. A61B 5/6833 600/365 |

OTHER PUBLICATIONS

Guardian Real-Time Continuous Glucose Monitoring System, User Guide, 2006, Medtronic MiniMed, Northridge, CA.

Dexcom G4 Platinum Professional Continuous Glucose Monitoring System, User's guide, 2014, Dexcom, IncG.

Dexcom G4 Platinum Continuous Glucose Monitoring System, Quick Start Guide, 2013, Dexcom, Inc., San Diego, CA.

Jonah Comstock, "Medtronic showcases smartphone-enabled continuous glucose monitoring," MobiHealthNews, http://mobihealthnews.com, Sep. 24, 2014.

* cited by examiner

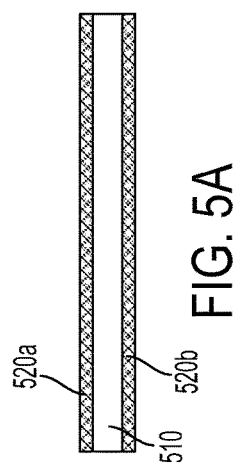
FIG. 5A
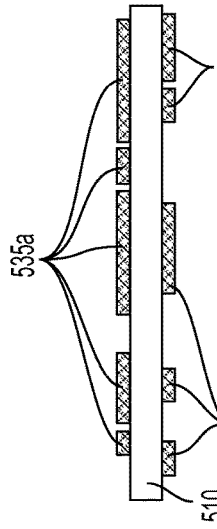
FIG. 5B
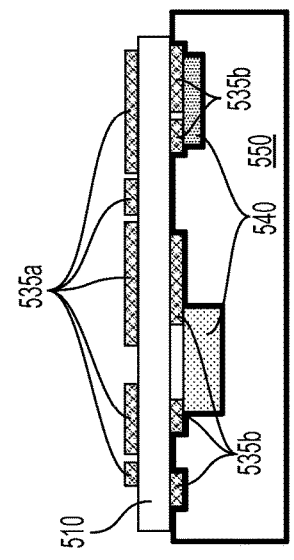
FIG. 5C
FIG. 5D
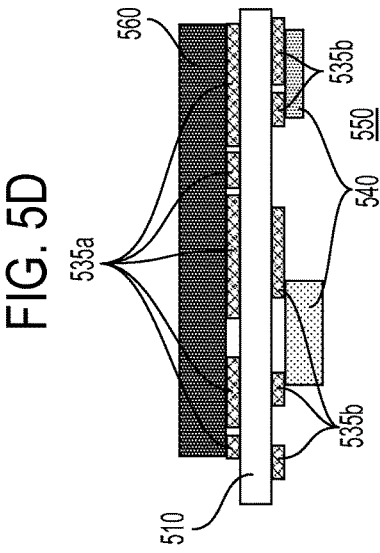
FIG. 5E
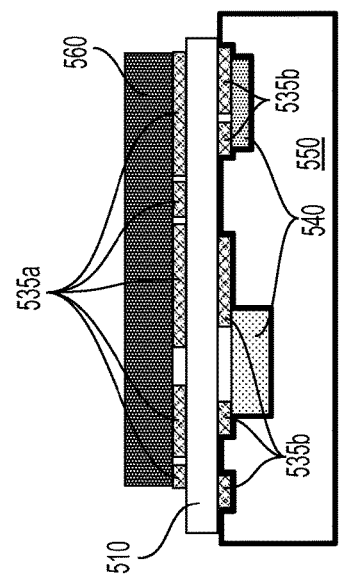
FIG. 5F

DISPLAY ON A BANDAGE-TYPE MONITORING DEVICE

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

Some embodiments of the present disclosure provide a body-mountable device including: (i) a flexible substrate that is configured to be mounted to a skin surface; (ii) a display disposed on the flexible substrate, wherein the display includes a plurality of electrodes disposed on the flexible substrate, a transparent conductive layer, and a display medium disposed between the plurality of electrodes and the transparent conductive layer; (iii) a sensor configured to detect a physiological property; and (iv) a controller that is disposed on the flexible substrate and that is electrically coupled to the display and the sensor. The controller is configured to perform controller operations including: (a) operating the sensor to detect the physiological property; and (b) operating the display to provide an indication related to the detected physiological property.

Some embodiments of the present disclosure provide a body-mountable device including: (i) a flexible substrate that is configured to be mounted to a skin surface; (ii) display means disposed on the flexible substrate, wherein the display means include a plurality of electrodes disposed on the flexible substrate, a transparent conductive layer, and a display medium disposed between the plurality of electrodes and the transparent conductive layer; (iii) sensing means configured to detect a physiological property; and (iv) controller means that are disposed on the flexible substrate and that are electrically coupled to the display means and the sensing means. The controller means are configured to perform controller operations including: (a) operating the sensing means to detect the physiological property; and (b) operating the display means to provide an indication related to the detected physiological property.

Some embodiments of the present disclosure provide a method that includes operating a body-mountable device mounted to a skin surface. The body-mountable device includes: (i) a flexible substrate that is configured to be mounted to a skin surface; (ii) a display disposed on the flexible substrate, wherein the display includes a plurality of electrodes disposed on the flexible substrate, a transparent conductive layer, and a display medium disposed between the plurality of electrodes and the transparent conductive layer; (iii) a sensor configured to detect a physiological property; and (iv) a controller that is disposed on the flexible substrate and that is electrically coupled to the display and the sensor. Operating the body-mountable device includes: (a) detecting, by the controller operating the sensor, the physiological property; and (b) providing, by the controller operating the display, an indication related to the detected physiological property.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5A is a cross-sectional view of an example body-mountable device during fabrication of the body-mountable device.

FIG. 5B is a cross-sectional view of the body-mountable device of FIG. 5A at a later stage in the fabrication of the body-mountable device.

FIG. 5C is a cross-sectional view of the body-mountable device of FIG. 5B at a later stage in the fabrication of the body-mountable device.

FIG. 5D is a cross-sectional view of the body-mountable device of FIG. 5C at a later stage in the fabrication of the body-mountable device.

FIG. 5E is a cross-sectional view of the body-mountable device of FIG. 5D at a later stage in the fabrication of the body-mountable device.

FIG. 5F is a cross-sectional view of the body-mountable device of FIG. 5E at a later stage in the fabrication of the body-mountable device.

DETAILED DESCRIPTION

Figure 1A:
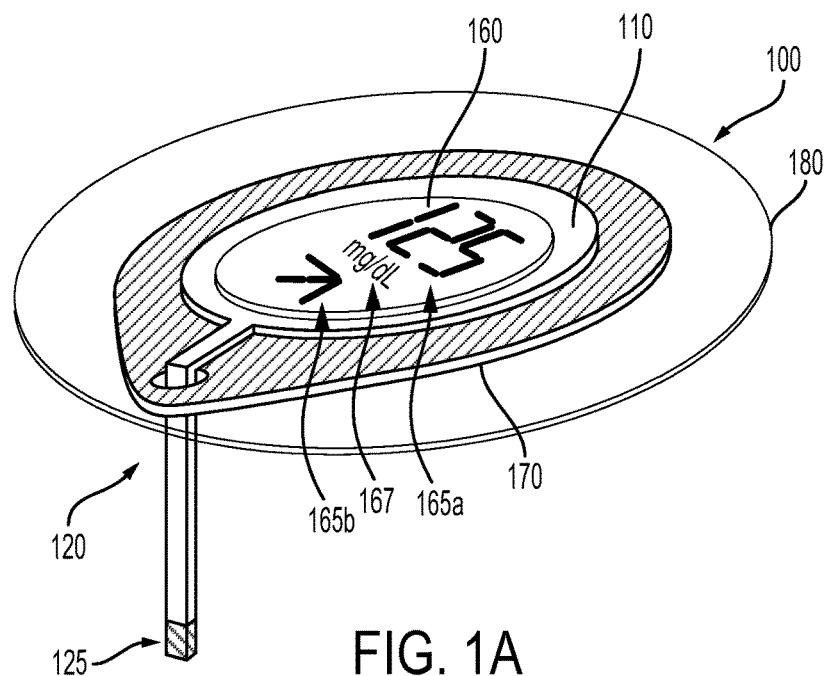
FIG. 1A is a top aspect view of an example body-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Some embodiments of the present disclosure provide a body-mountable device configured to be mounted to a skin surface of a living body (e.g., to skin of the upper arm or abdomen of a person), with one or more sensors for quantitatively or qualitatively detecting one or more physiological properties (e.g., a heart rate, a temperature, a concentration of glucose or some other analyte in interstitial fluid or some other fluid) of the living body. Further, elements of the body-mountable device are disposed on a flexible substrate that is configured to be mounted to the skin surface (e.g., by use of glue, tape, dry adhesive, or other adhesive means). Such a body-mountable device further includes a display that is disposed on the flexible substrate and that is configured to present outputs to the user, e.g., to display information about the detected physiological properties.

The flexibility of the flexible substrate (and of the body-mountable device overall) could provide a sensing platform that minimally interferes with activities of a body to which the sensing platform is mounted and/or that can be mounted to a body comfortably for protracted periods of time. This could include the flexible substrate and/or the sensing platform being sufficiently flexible that the flexible substrate complies with the shape of the skin surface and deforms with changes in the shape of the skin surface. Those of skill in the art will recognize that the sensing platform described herein may be provided in devices that could be mounted on a variety of portions of the human body to measure a variety of physiological properties of the human body (e.g., concentrations of a variety of analytes in a variety of fluids of the body, temperature, galvanic properties, ECG, muscle activity). Those of skill in the art will also recognize that the sensing platform described herein may be provided in devices that could be mounted in locations other than locations on a human body, e.g., locations on an animal body, locations that are part of a natural or artificial environment.

The display could be configured in a variety of ways to provide a variety of indications. In some examples the display could be a multi-segment display (i.e., a display configured to control a color, brightness, reflectivity, or other optical property of a plurality of disjoint areas or segments of the display), e.g., a multi-pixel display configured to indicate characters, numerals, images, or other information by controlling the color, reflectivity, or other properties of each of the pixels of the multi-pixel display. In some examples, a portion of a multi-segment display could be configured as a numerical multi-pixel display (e.g., including one or more multi-segment numerals whose segments could be used to indicate respective digits of a number). For example, a portion of a multi-segment display could include three seven-segment numerals and could be used to indicate three digits of a detected value of a physiological property (e.g., three digits of a detected blood glucose level). In some examples, a portion of a multi-segment display could be configured as a multi-segment trend indicator (e.g., two or more segments configured to indicate two or more arrows pointing in respective different directions) that could be used, e.g., to indicate an increasing or decreasing trend over time in the value of a detected physiological property.

The sensing platform could include other output components in addition to the display. Such an output component could include light-emitting elements (e.g., LEDs, OLEDs), color-changing elements (e.g., e-ink elements or displays, LCDs), haptic elements (e.g., vibrators, buzzers, electrohaptic elements), acoustical elements (e.g., buzzers, speakers), or some other elements configured to indicate some information, e.g., to a user. The display and/or other output component(s) could include flexible elements.

A display as described herein could include a variety of components configured in a variety of ways. In some examples, the display could include a display medium disposed between electrodes. A property of the display medium (e.g., a color, a reflectivity, an amount of light emitted from the display medium, an amount of twisting of polarized light) could be related to electrical fields and/or currents applied to the display medium by the electrodes disposed on either side of the display medium. An optical property of a portion (e.g., a segment) of the display (e.g., a color, a reflectivity) could be controlled by applying an electrical field and/or current to the display medium proximate the portion of the display (e.g., by applying a voltage and/or current to one or more electrodes corresponding to the portion or segment of the display). In some examples, the display could include a plurality of electrodes located on a first side of the display medium (e.g., each electrode could correspond to a segment of a multi-segment display) and a single electrode (e.g., a layer of transparent conductive material) located on the opposite side of the display medium. Other configurations of the display are anticipated.

In an example, the display medium could be a liquid crystal, and a color of a segment of the display could be controlled by applying an electric field to the liquid crystal using one or more electrodes corresponding to the segment of the display. A color or brightness of a segment of the display could be controlled by applying an electric field to the liquid crystal using one or more electrodes corresponding to the segment of the display. In another example, the display medium could include charged pigment particles (e.g., charged particles of titanium dioxide) disposed in a carrier medium or other material. The reflectivity or color of the display medium could be related to the location of such pigment particles within the display medium (e.g., particles of white titanium dioxide being located proximate to an outer surface of the display medium could cause the display medium to be more reflective and/or more white than when such pigment particles being located deeper in the display medium). A color or brightness of a segment of such a display could be controlled by applying a voltage between electrodes corresponding to the segment of the display; an electric field related to the applied voltage could cause charged pigment particles to move within proximate regions of the display medium (e.g., regions proximate the segment of the display).

The sensing platform could include an input component configured to detect a variety of inputs. The input component could be configured to detect sound (e.g., voice commands), motions of the device (e.g., a gesture that includes motion of the skin surface to which the sensing platform is mounts), contact between the sensing platform and a finger or other portion of a user's body, or some other inputs. For example, the input component could be configured to detect a location, motion, pressure, gesture, or other information about objects (e.g., a finger or other body part) near the sensing platform. The input component could include a capacitive touch sensor configured to detect a single touch, multiple touches, gestures, swipes, or other inputs. The input component could be a flexible component. In some examples, the input component could include one or more elements in common with the display. For example, an electrode of the display could also be used to detect a capacitance related to the proximity or other properties of a finger proximate the electrode (e.g., an electrode of the display could form part of a capacitive touch sensor). In some examples, the display could be operated to provide an indication of a detected physiological property or other information in response to an input received using the input component (e.g., responsive to a finger press). The sensing platform could operate and/or perform other functions responsive to inputs received using the input component.

The sensing platform could include a variety of sensors configured to detect a variety of physiological properties and/or properties of the environment of the sensing platform. In some examples, the sensor could include an analyte sensor configured to detect an analyte (e.g., glucose) in a fluid on or within the skin surface to which the sensing platform is mounted (e.g., interstitial fluid within or beneath the skin). In such examples, the sensor could include two or more electrodes configured to detect the analyte electrochemically (e.g., potentiometrically or amperometrically), a light sensor configured to detect the analyte optically (e.g., by illuminating and/or detecting light emitted from an analyte-sensitive substance that has an optical property related to the analyte), or other components configured to detect the analyte by some other means. The sensor could be disposed on a sensor probe that is configured to penetrate the skin (e.g., to a specified depth within the skin) such that the sensor can measure an analyte in a fluid within the skin. The sensor probe could be configured to pierce the skin (e.g., could be sufficiently rigid and/or sharpened such that the sensor probe can be driven into the skin). Additionally or alternatively, the sensor probe could be configured to pierce and/or penetrate the skin in combination with an insertion device. One or more sensors could be disposed at the end of such a sensor probe, at one or more additional locations along the length of such a sensor probe, and/or at some other location of a sensing platform as describe herein.

A sensing platform can include a power source, electronics, and an antenna all disposed on the flexible substrate configured to be mounted to skin of a living body. The electronics can operate one or more sensors (e.g., a sensor disposed at the distal end of a sensor probe) to perform measurements of an analyte (e.g., to measure the concentration of the analyte in interstitial fluid within or beneath the skin) or detect some other physiological properties. The electronics could additionally operate the antenna to wirelessly communicate the measurements from the sensor or other information to an external reader or some other remote system via the antenna. One or more of the power source, antenna, electronics, or other components of the sensing platform could be flexible; for example, the power source could include a thin, flexible lithium ion battery, zinc battery, or some other type of battery. In some examples, one or more of the power source, antenna, electronics, or other components of the sensing platform could be sufficiently flexible to allow for flexibility of the overall sensing platform and/or of elements of the sensing platform that are able to be mounted to skin (e.g., to provide greater comfort and/or to minimize effect on user activities when mounted to skin of a user).

Batteries of a sensing platform as described herein could be single-use or could be rechargeable. Rechargeable batteries could be recharged by power provided by radio frequency energy harvested from an antenna disposed on the flexible substrate. The antenna can be arranged as a loop of conductive material with leads connected to the electronics. In some embodiments, such a loop antenna can also wirelessly communicate the information (e.g., measurements of the analyte made using a sensor of the sensing platform) to an external reader (e.g., to a cellphone) by modifying the impedance of the loop antenna so as to modify backscatter radiation from the antenna. Additionally or alternatively, the sensing platform could include a chip, dipole, or other type of antenna for transmitting and/or reflecting RF energy to indicate information to an external reader. Further, such antennas could be used to transfer additional information, e.g., to indicate a temperature, light level, or other information detected by the sensing platform, to receive commands or programming from an external device, or to provide some other functionality.

It should be understood that the above embodiments, and other embodiments described herein, are provided for explanatory purposes, and are not intended to be limiting.

II. EXAMPLE FLEXIBLE BIOSENSOR PLATFORM

Figure 1B:
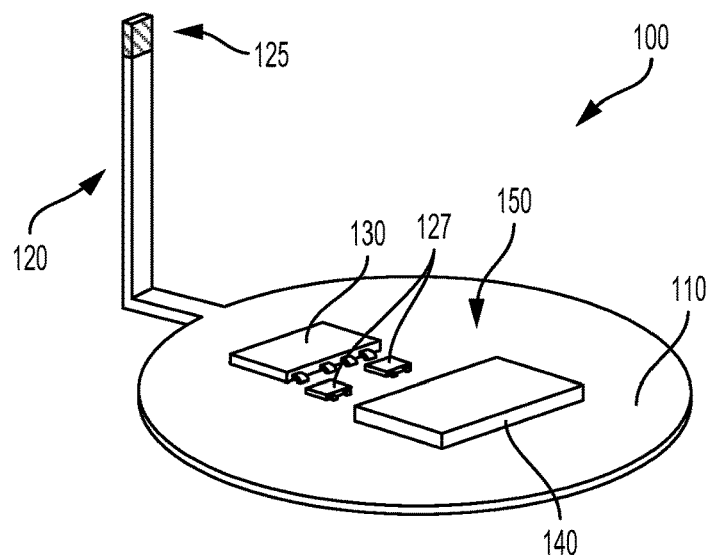
FIG. 1B is a bottom aspect view of the example body-mountable device shown in FIG. 1A.
Figure 1C:
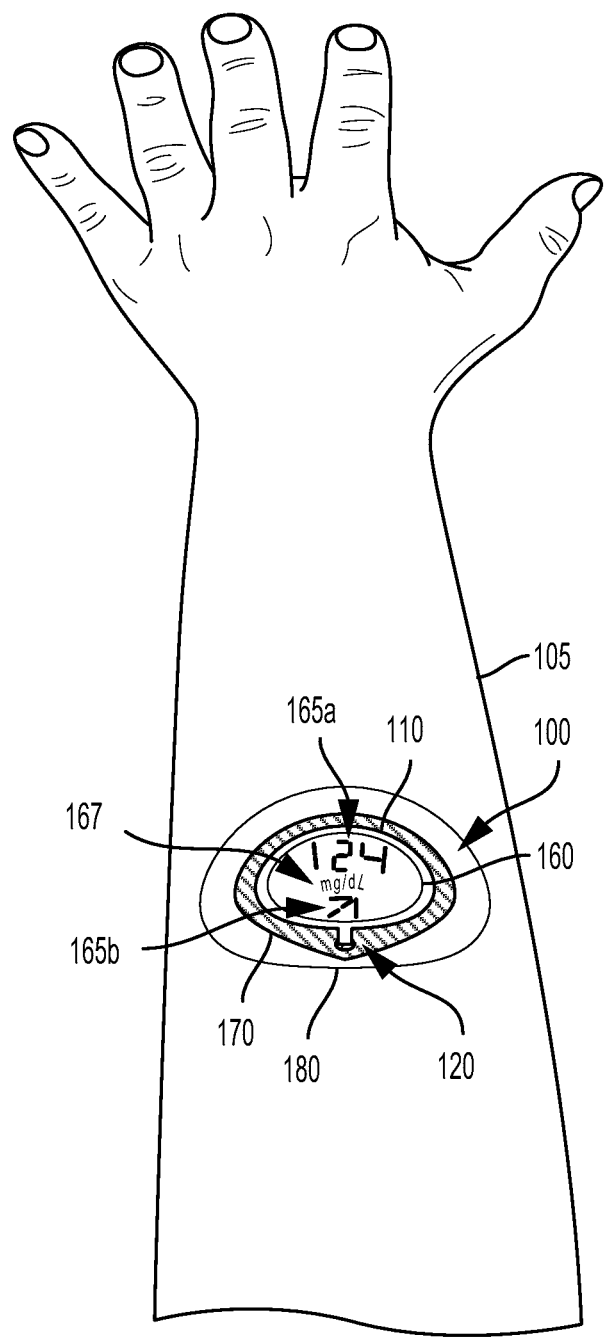
FIG. 1C is an aspect view of the example body-mountable device shown in FIGS. 1A and 1B when mounted to a body.

FIG. 1A is a top view of an example body-mountable sensing platform 100. FIG. 1B is a bottom view of the example body-mountable sensing platform 100 shown in FIG. 1A. FIG. 1C illustrates the example body-mountable sensing platform shown in FIGS. 1A and 1B mounted to skin of an arm 105. It is noted that relative dimensions in FIGS. 1A, 1B, and 1C are not necessarily to scale, but have been rendered for purposes of explanation only in describing the arrangement of the example body-mountable sensing platform 100. The body-mountable device 100 is formed of a flexible substrate 110 shaped (as an illustrative example) as a circular disk. A display 160 is disposed on the flexible substrate 110 and is configured to provide a visual indication (e.g., to change a color, to emit light, or to otherwise provide a visual indication) of some information (e.g., to display a charge status of the sensing platform, to provide an indication of a value of a property measured by the sensing platform, to provide a visual indication of an alert state determined by the sensing platform).

A sensor probe 120 extends from the flexible substrate 110 and is configured to penetrate a skin surface (e.g., to penetrate into skin of the upper arm (e.g., 105) or abdomen of a human body). An analyte sensor 125 is disposed at a distal end of the sensor probe 120. The analyte sensor 125 is configured to detect an analyte (e.g., glucose) in interstitial or other fluids under and/or within the skin when the sensor probe 120 penetrates the skin. An optical sensor 127 is also included to optically detect one or more properties of skin (e.g., by illuminating and/or detecting light emitted from the skin to detect an optical property, e.g., a color, reflectivity, or other properties).

A moisture-wicking polymer layer 170 is provided, on the underside of the flexible substrate 110. The moisture-wicking polymer layer 170 is configured to draw moisture away from the skin and/or from the base of the sensor probe 120 when the sensing platform 100 is mounted to skin (e.g., to the arm 105). The moisture-wicking polymer layer 170 could be comprised of a soft polyester or some other flexible polymer configured to draw moisture away from skin. The moisture-wicking polymer layer 170 could include a plurality of woven, crosslinked, or otherwise connected fibers of polymer material. Additionally or alternatively, the moisture-wicking polymer layer 170 could include one or more pieces of a microporous polymer material.

An adhesive layer 180 is disposed over the display 160, the flexible substrate 110, and the moisture-wicking polymer layer 170. The adhesive layer 180 is provided to mount the flexible substrate 110 and other components of the sensing platform 100 disposed thereon to a skin surface. The adhesive layer 180 and moisture-wicking polymer layer 170 are not shown in FIG. 1B, to simplify illustration of elements of the body-mountable sensing platform 100 that are disposed on the bottom surface 150 of the flexible substrate 110.

The body-mountable sensing platform 100 additionally includes electronics 130 disposed on the flexible substrate 110 and configured to provide various applications of the sensing platform 100 including, e.g., operating the analyte sensor 125 to detect an analyte, operating the optical sensor 127 to detect an optical property of skin, operating some other sensor of the sensing platform 100 to detect some other property or variable, receiving inputs from a user (e.g., using a capacitive touch sensor or other element of a user interface, not shown), providing an indication of information to a user (e.g., using the display 160), recording information (e.g., user inputs, measured concentrations of the analyte or other measured physiological properties) in a memory of the electronics 130, and communicating information (e.g., by using an antenna to wirelessly indicate such information) to an external system. The antenna (not shown) could be configured as a loop antenna on one or both surface of the flexible substrate 110 (e.g., encircling the electronics 130 and/or display 160), or the antenna could be configured as a chip antenna or some other configuration. A battery 140 is provided to power the body-mountable sensing platform 100 (e.g., to power the electronics 130). Components (e.g., antennas, batteries, electronics) could additionally or alternatively be disposed on the top surface of the flexible substrate 110 (i.e., the surface of the flexible substrate 110 opposite the bottom surface 150).

The flexible substrate 110 is configured to be mounted to a skin surface. In the example shown in FIG. 1C, this includes a layer of adhesive 180 being provided to adhere the flexible substrate 110 to a skin surface of the arm 105. Additional or alternative means could be provided to mount the flexible substrate 110 to a skin surface. For example, a liquid or gel adhesive could be applied to the skin surface and/or to the flexible substrate 110 to mount the flexible substrate 110 to the skin surface. The flexible substrate 110 could be placed on the skin surface and secured using tape or other adhesives. In some examples, the body-mountable sensing platform 100 could include a dry adhesive configured to removably mount the flexible substrate 110 to a skin surface. Other means for mounting the flexible substrate 110 or other elements of the body-mountable sensing platform 100 to a skin surface or to other elements or aspects of a living body are anticipated. Further, in some embodiments, a body-mountable sensing platform 100 could be provided that is configured to be placed proximate a target fluid (e.g., interstitial fluid, synovial fluid, blood, tears, saliva, mucus) without mounting to a skin surface or other tissue surface. For example, a body-mountable sensing platform 100 as described herein could be configured to be placed between the teeth and cheek of a living body, on the eye of a living body, or at some other location of a living body without being mounted to a particular tissue surface.

Body-mountable sensing platforms as described herein (e.g., 100) could be mounted to skin at a variety of different locations of a body. Such locations could be selected to provide access to a particular portion of skin and/or a particular type or portion of tissue (e.g., to provide access to a portion of subsurface vasculature). Additionally or alternatively, such locations could be selected to minimize discomfort caused by the sensing platform being mounting to skin for a protracted period of time (e.g., by being mounted to a portion of skin that includes fewer nerve endings and/or that is minimally strained during the performance of activities of daily living). Further, where a sensing platform includes an input component, an output component, and/or some other user interface means, such locations could be selected to provide convenient interaction between a wearer and the user interface (e.g., locations that allow easy contact between a finger of a user and the sensing platform, location that allow easy viewing of visually-indicating output components of the sensing platform). Such locations could include locations on the arms or abdomen of a user.

FIG. 1C illustrates such a location, showing the body-mountable sensing platform 100 mounted to skin of the arm 105. The flexible substrate 110, and the sensing platform as a whole 100, are sufficiently flexible that the sensing platform 100 conforms (i.e., curves) to the shape of the surface of the skin to which the flexible substrate 110 is mounted (e.g., by the adhesive layer 180). This could include the display 160, moisture-wicking polymer layer 170, adhesive layer 180, and/or other components (e.g., electronics 130) being sufficiently flexible to conform to the shape of the surface of the skin. Additionally or alternatively, one or more components of the sensing platform 100 could be rigid and shaped and/or sized such that, when disposed on the flexible substrate 110, the sensing platform 100 as a whole can conform to the shape of 'the surface of the skin to which the flexible substrate 110 is mounted.

The flexible substrate 110, display 160, moisture-wicking polymer layer 170, adhesive layer 180, and/or other elements of the body-mountable sensing platform 100 can have a thickness, shape, composition, rigidity, compliance, elasticity, viscoelasticity, and/or other properties specified such that the flexible substrate 110 can be mounted to a skin surface of a living body and further such that such mounting minimally interferes with activities of the living body (e.g., motions of the living body). This could include the flexible substrate 110 and components disposed thereon (e.g., the display 160) being sufficiently flexible that mounting of the flexible substrate 110 to the skin surface causes a minimum of discomfort. The body-mountable sensing platform 100 could be sufficiently flexible that the flexible substrate 110 and components mounted thereto/dispose therein conform to and move with the shape of the skin surface (e.g., as illustrated in FIG. 1C). This could include elements disposed on/in the flexible substrate 110 being flexible. For example, elements (e.g., elements of the display 160, electronic components, input components, output components, sensors) could include or be composed of flexible polymers, flexible metal films, traces, and/or electrodes (e.g., metal traces or electrodes formed on the flexible substrate 110), or other flexible materials and/or materials formed to be flexible (e.g., a rigid material formed to include a strain relief, to be thin or narrow, or otherwise formed such that an element composed of the rigid material is functionally flexible).

Additionally or alternatively, rigid components (e.g., rigid electronic components, rigid integrated circuits) could be mounted to the flexible substrate 110 such that the body-mountable sensing platform 100 is, overall, flexible. This could include the rigid components being small, the rigid components being separated by a specified distance on the flexible substrate 110, the rigid components having a long shape and being disposed parallel to each other on the flexible substrate 110 such that the body-mountable sensing platform 100 is flexible in a direction perpendicular to the orientation of the rigid components, or some other configuration of the flexible substrate 110 and components disposed thereon/therein such that the body-mountable sensing platform 100 is flexible (e.g., such that the body-mountable sensing platform 100 is complaint and conforms to a skin surface to which the body-mountable sensing platform 100 is mounted, such that the body-mountable sensing platform 100 being mounted to the skin surface minimally interferes with activities of a body/causes minimal discomfort).

The flexible substrate 110 could be composed of polyimide, polyethylene terephthalate, or some other flexible polymeric or other material. The flexible substrate could have a thickness less than approximately 100 microns. Further, the flexible substrate 110 could have a size specified to minimally interfere with activities of the living body. For example, the flexible substrate 110 could have size (e.g., a diameter of a circular portion, as illustrated in FIGS. 1A, 1B, and 1C) less than approximately 11 millimeters. Diameter and thickness values are provided for explanatory purposes only. Further, the shape of the flexible substrate 110 could be different from that illustrated in FIGS. 1A and 1B or elsewhere herein; for example, the flexible substrate 110 could have an elongate shape, a square or rectangular shape, or some other shape according to an application. For example, the flexible substrate 110 could have an elongate shape to provide sufficient area for disposition of electronics, batteries, user interface components (e.g., touch sensor electrodes, flexible display elements), antennas, or other components on the flexible substrate 110 while minimally impeding motion and/or deformation of the skin surface to which the flexible substrate 110 is mounted (e.g., by being formed and/or mounted to the skin surface such the orientation of the elongate shape of the flexible substrate 110 is perpendicular to a direction of strain of the skin surface).

One or more surfaces of the flexible substrate 110 (e.g., the bottom surface 150) could be used as a platform for mounting electronics such as chips (e.g., via flip-chip mounting) and for patterning conductive materials (e.g., via deposition techniques) to form electrodes, antenna(e), and/or connections. The composition of the flexible substrate 110 could be chosen to allow for the formation and/or disposition of such elements of the body-mountable sensing platform 100. For example, the flexible substrate 110 could be composed of polyimide, polyethylene terephthalate, or some other polymeric and/or metallic material(s) such that metal contacts, traces, and interconnects can be patterned directly on the surface of the flexible substrate 110 (e.g., by sputtering, CVD, or some other deposition process) and/or on a coating or layer formed on one or more surfaces of the flexible substrate 110. Further, such patterned structures and/or other elements disposed on the flexible substrate 110 (e.g., electronics 130, optical sensor 127, battery 140, display 160, moisture-wicking polymer layer 170, antennas) could, in combination with the flexible substrate 110, have a thickness or other property specified to provide the overall body-mountable sensing platform 100 with flexibility. For example, the flexible substrate 110 in combination with electronics 130, display 160, moisture-wicking polymer layer 170, optical sensor 127, and battery 140 disposed thereon could have a thickness less than approximately 0.5 millimeters.

One or more components of a sensor, display, input component, output component, or other elements of the body-mountable sensing platform 100 could be formed directly on the flexible substrate 110 as a deposited metal film, dielectric material or coating, or other deposited material. For example, one or more electrodes of a capacitive touch sensor (e.g., a sensor configured to detect the presence, location, motion, or other properties of a fingertip, other body part, or other objects proximate and/or in contact with the capacitive touch sensor) could be formed on the flexible substrate 110 to provide a flexible input component (i.e., the capacitive touch sensor). Electrodes or other elements of a resistive touch sensor, a conductive touch sensor, a pressure sensor that could be operated to receive inputs from a user, an electrohaptic output component (e.g., two or more electrodes configured to be in contact with skin when the body-mountable sensing platform 100 is mounted to the skin and to deliver an electro-haptic stimulus to the skin through the two or more electrodes), an electrochemical analyte sensor, a galvanic skin resistance or potential sensor, an electromyogram (EMG) or electrocardiogram (ECG) sensor, or some other components could be formed by depositing metals or other materials on the flexible substrate 110.

Further, elements of the display 160 could be formed on or within the flexible substrate 110. For example, organic LED light-emitting elements (e.g., individual OLED indicator lights, OLED displays) or other flexible semiconductors could be deposited and/or formed on or within the flexible substrate 110. Additionally or alternatively, such elements (or other components of a body-mountable sensing platform 100) could be formed separately from the flexible substrate 110 and deposited and/or disposed on the flexible substrate 110 (e.g., using an adhesive, by welding, by reflow soldering between contacts of the element(s) and corresponding metallic pads or traces formed on the flexible substrate 110). In a particular example, a plurality of electrodes of the display 160 could be formed on the flexible substrate 110. Each formed electrode could correspond to an individually-controlled element of the display, e.g., individual pixels of a multipixel display configured to provide images, characters, and numerals. For example, each electrode formed on the flexible substrate 110 could correspond to a segment of a multi-segment display, e.g., a multi-segment numerical display configured to provide one or more seven-segment digit indications. A display medium (e.g., a layer of liquid crystal, a layer of charged pigment disposed in a carrier medium, a layer of some other material having a color, intensity of emitted light, reflectivity, or other optical property that can be controlled by voltages, current, charges, and/or electric fields applied thereto) could be adhered to the formed electrodes such that a voltage and/or current could be applied to the electrodes to control a color, brightness, or other optical property of a corresponding region of the display medium (e.g., a region corresponding to a segment of a multi-segment display formed from the display medium).

As illustrated in FIGS. 1A and 1C, outputs provided by the display 160 could indicate information about the body-mountable sensing platform (e.g., a battery charge status, an amount of free memory of the device) and/or information detected by the device (e.g., a concentration of an analyte or value of some other property sensed by one or more sensors of the device). Visual indications provided by the sensing platform 100 (e.g., numerals, letters, other characters, images, trend-indicating arrows or other symbols) could be generated by operating the display 160 (e.g., by applying a voltage and/or current to one or more electrodes of the display 160 to change a color, emit a light, or provide some other visual indication) and/or could be static indications printed, embossed, inscribed, or otherwise formed on the display 160, flexible substrate 110, adhesive layer 180, or other elements of the device 100. Further, an output component of the sensing platform 100 (not shown) could be configured to provide an indication of information by emitting sounds, by presenting a haptic stimulus to a user (e.g., a vibration, an electrical stimulus, an increased or decreased temperature), or by some other method.

Provided indications could include alerts generated by the device 100, e.g., alerts based on a determination that a user is experiencing an adverse health condition (e.g., determined based on a property detected using sensors 125, 127 of the device 100). In some examples, an output component could be operated to indicate information in response to a received input (e.g., the display 160 could be operated to provide an indication of information in response to a received input), in response to a determined alert condition (e.g., an alert sound could be indicated in response to a determination that a user requires medical intervention), or in response to some other event or input (e.g., an alert generated by a remote system in communication with the body-mountable sensing platform 100).

The display 160 could include an OLED, LED, liquid crystal, electronic paper, or other type of display medium configured to emit a light, change a color, or otherwise visually indicate some information. In some examples, a body-mountable sensing platform 100 could include one or more discrete light emitters (e.g., LEDs, OLEDs) configured to emit light to indicate some information (e.g., to indicate an alert, to indicate a battery status, to indicate some information related to a property detected by sensors, e.g., 125, 127, of the device 100). Additionally or alternatively, a device 100 could include a piezo element, a speaker, or some other element configured to emit a sound (e.g., to beep, to play an alert sounds, to play a recorded message). In some examples, a body-mountable sensing platform could include a haptic element configured to provide an indication of some information by delivering a haptic stimulus (e.g., vibration, heat, pain, touch) to a user. Such a haptic element could include a vibrator (e.g., a motor configured to drive an unbalanced mass), a piezo element configured to couple vibrations into skin, two or more electrodes configured to deliver an electro-haptic stimulus into skin, or some other components configured to deliver a haptic stimulus to a user.

In the illustrated example, a portion of the display 160 is configured as a multi-segment numerical display 165*a*. As illustrated, the multi-segment numerical display 165*a* of the display 160 is configured to have two seven-segment numerals that can be operated to indicate numerals from 0 to 9 and a two-segment numeral that can be operated to indicate a '1' numeral. Each segment of the multi-segment numerical display 165*a* corresponds to at least one respective electrode of the display (e.g., an electrode formed on the flexible substrate 110). For example, a particular segment could correspond to a particular electrode and the color or other optical properties of the particular segment could be controlled by applying a voltage between the particular electrode an a corresponding electrode opposite a layer of display medium of the display (e.g., an electrode corresponding to the particular segment, an electrode corresponding to a larger region of the display 160, e.g., an electrode disposed across substantially all of the display 160).

A context indication 167 is provided on sensing platform 100 proximate the multi-segment numerical display 165*a*. The context indication 167 indicates the units of a numerical indication provided by the multi-segment numerical display 165*a*. As illustrated, the context indication 167 indicated that the multi-segment numerical display 165*a* is indicated a detected value of 125 milligrams per deciliter (e.g., a blood glucose level detected by the sensor 125 is approximately 125 milligrams per deciliter). The context indication 167 could be a static indication, e.g., printed, stamped, or otherwise formed in or on the display 160, flexible substrate, adhesive layer 180, or some other element(s) of the sensing platform 100 such that the context indication 167 is visible to a user. Additionally or alternatively, all or part of the context indication 167 could be provided by operating the display 160, e.g., by applying a voltage and/or current to one or more electrodes of the display 160.

In the illustrated example, a further portion of the display 160 is configured as a multi-segment trend display 165*b*. As illustrated, the multi-segment trend display 165*b* of the display 160 has several segments that that can be operated to indicate an increasing or decreasing trend, e.g., across multiple detected values of a physiological property detected by the sensor 125. The multi-segment trend display 165*b* is configured to indicate a trend by indicating an upward- or downward-pointing arrow, respectively. Each segment of the multi-segment trend display 165*a* corresponds to at least one respective electrode of the display (e.g., an electrode formed on the flexible substrate 110).

As illustrated, the display 160 (e.g., the multi-segment numerical display 165*a* and the multi-segment trend display 165*b*) is being operated to illustrate an analyte concentration (detected using, e.g., the analyte sensor 125) and a change in the analyte concentration over time (e.g., between a most-recent detected value of the analyte concentration and a second-most-recent detected value of the analyte concentration). The display 160 could be configured to additionally present some other information, e.g., a charge state of a the battery 140, an amount of data storage that is available to record detected analyte concentrations or other information, an alert state determined by the device (e.g., an alert state related to an adverse health state related to a detected value of the analyte concentration), or some other information. Further, the context indication 167 could be part of a multi-segment display configured to provide a variety of different indications, e.g., corresponding to different uses of the multi-segment numerical display 165*a* and/or multi-segment trend display 165*b* to indicate information.

For example, the context indication 167 could be a multi-segment display having respective different segments (and corresponding different electrodes), e.g., a segment corresponding to the illustrated "mg/dL" context indication 167, that could be operated during respective different periods of time to indicate respective different contexts for numerals and/or trends indicated by the multi-segment numerical display 165*a* and/or multi-segment trend display 165*b*, respectively, during the respective different periods of time. For example, the illustrated "mg/dL" could be indicated during a first period of time when the multi-segment numerical display 165*a* is operated to display a detected analyte concentration in milligrams per deciliter. During a second period of the context indication 167 could be operated to indicate "% BATT" (not shown) when the multi-segment numerical display 165*a* is operated to display a battery charge status of the flexible battery 140.

Note that the illustrated elements and/or operation of the display 160 are intended as a non-limiting example embodiment. A display (or other aspects of a user interface of the sensing platform 100, e.g., one or more indicator LEDs, electroluminescent elements, or other output components) could be configured differently and/or include different or additional means for indicating information. As shown in FIGS. 1A and 1C, the display 160 is configured to provide indications by controlling the color of regions of the display 160 (e.g., regions corresponding to segments and/or electrodes of the display 160) between dark and light (e.g., between substantially black and substantially white). However, the display 160 could be configured to be a color display (e.g., by including a plurality of pixels, segments, electrodes, or other elements controlling the color of respective regions of the display 160). Additionally or alternatively, the display 160 could be configured to emit light. In some examples, this could include segments or other elements of the display (e.g., material of a display medium of the display 160) being configured to individually emit light. Additionally or alternatively, the sensing platform 100 could include a backlight (e.g., layer of electroluminescent material disposed as part of and/or beneath the display 160) configured to emit light through the display 160 and the display 160 could be configured to provide indications (e.g., multi-segment numerical indications) by controlling a pattern of the light emitted by the backlight that is visible to a user (e.g., by controlling a transparency or other optical property of regions or segments of the display 160).

In some examples, the display 160 could be configured and/or operated to consume very little power. For example, the sensing platform 100 could be powered by the flexible battery 140 and the display 160 could be configured and/or operated such that the flexible battery 140 can power the sensing platform 100 for an extended period of time, e.g., several days, two weeks, or some other period of time. In some examples, this could include operating the display 160 intermittently, e.g., only operating the display 160 to indicate information (e.g., measured analyte concentrations) during specified periods of time, e.g., in response to a user providing an input (e.g., a press or touch of a finger against the sensing platform 100 detected by a capacitive touch sensor) the display 160 could be operated to provide such an indication for a specified period of time.

Further, the display 160 could be configured to operate using a low power budget. For example, the display 160 could be a liquid-crystal display, an electronic paper display, or some other display technology configured to provide a visual indication using little power. Such operation can use power only when changing an indication provided by the display 160, e.g., to change the location, orientation, or other properties of the disposition of charged pigment particles within a display medium of the display 160 (e.g., by applying a voltage and/or current to regions or segments of the display 160). Such a provided indication could remain on the display 160 until some specified condition is met (e.g., until an updated indication is requested). Additionally or alternatively, the display 160 could be blanked (e.g., set to a single color/reflectivity or otherwise set to some default display state) after a specified period of time passes from a time when the display 160 is operated to provide an indication.

In a particular example, the display medium of the display 160 could include charged pigment particles disposed in a carrier fluid or other medium (e.g., a liquid polymer, a colored hydrocarbon oil). For example, the display 160 could be an electronic paper display. The location, orientation, and/or disposition of the charged pigment particles within the display medium can be controlled by applying electric fields to the display medium (e.g., by applying specified voltages between electrodes and/or transparent conductive layer(s) of the display 160) to control the color and/or reflectivity of segments or regions of the display. In some examples, the display medium could include a plurality of hollow beads (e.g., hollow beads composed of a polymer and having diameters of approximately 30 microns) within which such charged particles, carrier fluids, and other display elements could be disposed. In such examples, the plurality of hollow beads could be disposed in a layer (e.g., disposed within a layer of polymer configured to contain the beads) such that the display medium is flexible and further such that the display medium can be cut or otherwise modified to assume a specified shape without forming any termination or seal at the edge of any such cuts, e.g., to prevent a fluid of the display medium from leaking out of the display.

In some examples, the charged pigment particles could be dipolar (i.e., individually having first ends that are positively charged and second ends that are negatively charged) and could have first and second halves having respective first and second colorations (e.g., black and white colorations, respectively). Application of an electric field to the charged pigment particles could control an orientation of the charged pigment particles (e.g., by applying an electric torque to the charged particles) thus controlling the color of a region of the display 160 by controlling which coloration of the charged particles is directed toward a user (i.e., toward an external surface of the display 160).

In some examples, the charged pigment particles could have a first coloration (e.g., white) and could be disposed in a substantially opaque carrier fluid, gel, or other medium having a second coloration (e.g., black) and through which the charged particles could be moved by application of electric fields (e.g., a hydrocarbon oil that intrinsically has the second coloration and/or to which a pigment having the second coloration has been added). Application of an electric field to the charged pigment particles could control a location of the charged pigment particles (e.g., by applying an electric force to the charged particles) thus controlling the color of a region of the display 160 by controlling the disposition of the charged pigment particles within the display medium. For example, regions of the display wherein the charged pigment particles are disposed proximate an external surface of the display 160 could have a coloration similar to the coloration of the charged pigment particles (e.g., white) while regions of the display wherein the charged pigment particles are disposed deeper within the display 160 could have a coloration similar to the coloration of the carrier fluid (e.g., black).

Further, the sensing platform 100 could include additional output components or other means for providing indications to a user. For example, the sensing platform 100 could include speakers, piezo elements, or acoustical elements or other means for generating sounds to indicate information (e.g., to beep, to generate a tone, to play a recorded and/or synthesized sound). The sensing platform 100 could include a vibrator, one or more electrodes configured to deliver an electro-haptic stimulus to skin, a heating element configured to heat skin, or some other haptic elements configured to deliver a haptic stimulus to a person.

Further, the sensing platform 100 could include means for receiving inputs (e.g., for detecting the presence of, location of, force exerted on the display 160 by, and/or motion of a fingertip or other body part of a user). The sensing platform 100 could include one or more electrodes, ultrasonic transducers, cameras, or other means configured to receive inputs by detecting a capacitance, a resistance, a conductance, or some other property related to the location, motion, and/or contact of a finger, body part, or other object proximate to or in contact with the user interface. Such input components could receive input by including one or more pressure sensitive elements configured to detect contact, pressure, force, or other properties of an interaction between the user interface and a finger, body part, or other object in contact with the user interface. Input components could include a microphone or other pressure transducing element configured to receive inputs by detecting sounds (e.g., vocal commands) produced by a user. The sensing platform 100 could include additional or alternative input and output components to those described herein.

Received inputs could include a location, pressure, duration, or other properties of a body part or other object being in contact with the sensing platform 100. Received inputs could include a direction of motion of a body part or some other gesture performed by the body part (e.g., upward, downward, or other motion relative to one or more elements of the sensing platform 100 (e.g., the display 160), a clockwise or counterclockwise motion relative to a capacitive touch sensor of the sensing platform 100 (e.g., around a periphery of the display 160). Received inputs could represent selection and/or operation of an element of the user interface (e.g., a 'button' of the user interface, an operational mode from a presented list of operational modes, an element representing an increment or decrement of a value) by a user. Received inputs could indicate a user's intent to change a value of a parameter of the sensing platform 100 (e.g., an upward motion could indicate the user's intent to increase a calibration parameter, while a downward motion could indicate the user's intent to decrease the calibration parameter), to change an operational mode of the sensing platform 100, or to affect some other operation of the sensing platform 100 and/or to indicate some other information (e.g., to indicate an emotional or physical state of a user, to indicate an activity performed by the user).

The sensing platform 100 could include a variety of input components configured to receive inputs. Such input components could be configured to detect a variety of properties of the sensing platform 100 (e.g., a temperature of the sensing platform, an effective capacitance of elements and/or regions of the sensing platform 100), of the environment of the sensing platform (e.g., a temperature of the environment of the sensing platform and/or skin to which the sensing platform 100 is mounted, an amount of light received by the sensing platform 100), and/or of objects (e.g., fingers) proximate the sensing platform 100. In some examples, the input component could include an accelerometer configured to detect the velocity, acceleration, or other properties of motion of the sensing platform 100 (e.g., to detect gestures or other inputs performed by a user by performing a motion of a body part to which the sensing platform 100 is mounted). In some examples, the input component could include one or more electrodes configured to detect a capacitance related to the presence, location, motion, or other properties of fingers, body parts, or other objects proximate the input component. The input component could include multiple such electrodes configured to detect the presence or other properties of body parts or other objects proximate the multiple electrodes, e.g., to detect interaction with (e.g., a finger pressing) a user interface element corresponding to one of the multiple electrodes. For example, the sensing platform 100 could include a set of electrodes configured to act as a set of capacitive 'buttons' of the user interface. In some examples, some or all of such electrodes or other components of an input component could also be components of the display 160. For example, a transparent conductor layer of the display 160 (configured, e.g., to apply a voltage and/or current to regions of a display medium of the display 160) could be used as an electrode of a capacitive touch sensor).

Alternatively, an input component could be configured to detect a pressure (e.g., a pressure exerted on the sensing platform 100 by a finger or other object), an amount of received light (e.g., an amount of ambient light received by a portion of the sensing platform 100 that is reduced due to occlusion by a finger or other object), a conductance between two or more electrodes (e.g., a conductance between two electrodes that is reduced due to the presence of a conductive finger or other object between the two electrodes), or some other property related to a received input.

In some examples, the input component could include one or more elements in common with a sensor of the body-mountable sensing platform 100. For example, a sensor of the device 100 could be configured to detect a temperature of skin to which the device 100 is mounted. Such a sensor could additionally be operated to receive inputs by detecting changes in the detected temperature (e.g., changes in the temperature of the skin and/or the temperature of the device 100) related to contact between a finger or other object and the device (e.g., due to an insulating effect of the presence of the finger or other object). In another example, a sensor of the device 100 could be configured to detect a conductance of skin to which the device 100 is mounted (e.g., by detecting a conductance between two electrodes in contact with the skin). Such a sensor could additionally be operated to receive inputs by detecting changes in the detected conductance related to pressure and/or forces exerted on the device 100 by a finger or other object (e.g., due an increase in the detected conductance related to improved electrical contact between electrodes of the sensor and the skin to which the device 100 is mounted related to the pressure and/or force exerted by the finger or other object).

Inputs received by one or more input components of the sensing platform 100 could be received and/or detected by the body-mountable sensing platform 100 and used to perform a variety of functions of the sensing platform 100. In some examples, providing an indication of information using the display 160 could be based on one or more received inputs. For example, a type of information indicated (e.g., battery charge status, free memory amount, a value of a detected property) could be based on received inputs. Further, such information could be indicated responsive to a received input. For example, the display 160 could be deactivated or otherwise placed in a low-power state until an input is received, at which time the display could be operated to indicate some information (e.g., a backlight could be activated, one or more OLED elements of a display could be lit, a liquid crystal display and/or electronic paper display could be operated to provide an indication).

Received inputs could indicate some information about a user and/or activities of a user and/or the environment of the user. For example, received inputs could correspond to an emotional or physical state of a user (e.g., nausea, malaise), activities of a user (e.g., that the user has performed exercise, consumed a meal, or received and/or taken a drug), or some other information. In some examples, received inputs could indicate one or more parameters that could be used by the sensing platform 100. For example, received inputs could represent a calibration value of a property detected by one or more sensors of the sensing platform 100 e.g., a blood glucose level detected using some other device. Such a received calibration value could be used to modify the operation of the sensing platform 100, e.g., to determine a value of glucose in the blood based on a measured value detected by the sensor 125.

The electronics 130 disposed on the flexible substrate 110 could include a variety of devices. For example, the electronics 130 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 110. Further, antennas, electrodes, capacitors, resistors, or other components could be formed from such traces or other interconnects formed on the surface of the flexible substrate 110. The electronics 130 can include logic elements configured to operate the analyte sensor 125 to detect an analyte, the optical sensor 127 to detect an optical property of skin, the display 160 to indicate some information, an antenna (e.g., a loop, dipole, or other type of antenna formed on the flexible substrate 110, a chip antenna disposed on the flexible substrate 110) to wirelessly indicate information (e.g., concentration levels about a detected analyte), and/or to provide other functions.

A loop, dipole, or other type of antenna can be one or more layers of conductive material patterned on a surface (e.g., 150) of the flexible substrate 110 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for an electrochemical analyte sensor, for a capacitive touch sensor of an input component, for one or more segments or other elements of a multi-pixel or otherwise configured display 160, etc.) can be formed from conductive materials patterned on the flexible substrate 110 by a process for precisely patterning such materials, such as deposition, lithography, etc. The conductive materials patterned on the flexible substrate 110 can be, for example, gold, platinum, palladium, titanium, carbon, aluminum, copper, silver, silver-chloride, conductors formed from noble materials, metals, combinations of these, etc.

The sensor probe 120 is an elongate element of the body-mountable sensing platform 100 that is configured to penetrate a skin surface such that the analyte sensor 125 located at the distal end of the sensor probe 120 is in contact with a fluid (e.g., interstitial fluid, blood) containing an analyte of interest (e.g., glucose) when the sensor probe 120 is penetrating the skin. For example, the sensor probe 120 could be more than approximately 2 millimeters long. The sensor probe 120 could have a length or other properties specified such that, when the sensor probe 120 penetrates skin and/or the flexible substrate 120 is mounted to a skin surface, a sensor (e.g., 125) or other element(s) disposed on the sensor probe 120 contacts tissue at a specified depth within the skin (e.g., tissue of the dermis of the skin, subcutaneous tissue). For example, the sensor probe 120 could have a length between approximately 500 microns and approximately 6000 microns. Further, the sensor probe 120 could have one or more dimensions specified to provide sufficient area for electrodes or other elements disposed on the sensor probe 120, to minimally interfere with the skin (e.g., by requiring a minimal incision or other alteration of the skin to provide for penetration of the sensor probe 120), or according to some other application. For example, the sensor probe 120 could have a width between approximately 25 microns and approximately 400 microns.

The sensor probe 120 could be composed of a variety of materials and elements formed by a variety of processes. The sensor probe 120 could be composed of a flexible material (e.g., polyimide) or a relatively inflexible material; further, a thickness, width, shape, or other properties of the sensor probe 120 could be specified to provide a degree of flexibility or inflexibility. For example, a flexible sensor probe 120 could have a width between approximately 25 microns and approximately 400 microns and/or a thickness less than approximately 100 microns.

In some examples, the sensor probe 120 could be formed from the same material as the flexible substrate 110; i.e., the sensor probe 120 could be an elongate portion of the flexible substrate 110 that extends from a portion of the flexible substrate 110 that is configured to be mounted to a skin surface and/or on which electronics 130 or other components are disposed. Alternatively, the sensor probe 120 could be attached to the flexible substrate 110. For example, the sensor probe 120 could include optical fiber(s), flexible element(s) (e.g., an elongate piece of polyimide or other polymeric or metallic substance), wire(s), elongate pieces of shaped silicon, or other elements adhered, welded, bonded, or otherwise attached to the flexible substrate 110.

Alternatively, such sensor probes could be used for other applications and/or in combination with components or devices other than a flexible substrate (e.g., 110) as described herein. For example, one or more sensors or other elements disposed on the sensor probe 120 could be used as part of an input component configured to receive inputs (e.g., one or more electrodes configured to detect a galvanic skin conductance, an EMG signal, or some other property related to a user input) and/or an output component configured to provide an indication of information (e.g., one or more electrodes configured to deliver an electro-haptic stimulus, a heater configured to deliver heat into skin to indicate some information or alert). Further, a body-mountable sensing platform as described herein could lack such a sensor probe, or could include more than one sensor probe.

The sensor probe 120 could be configured to pierce skin to allow the sensor probe 120 to penetrate the skin and dispose the analyte sensor 125 and/or other elements disposed on the sensor probe 120 in contact with interstitial or other fluids within the skin. For example, the sensor probe 120 could be sharpened, could include one or more rigid materials to facilitate application of force to the sensor probe 120 to pierce the skin (e.g., stainless steel tubes, rods, sheets, and/or needles), or could be otherwise configured to pierce skin. In some examples, the sensor probe 120 could include materials having a stiffness or some other property that changes to allow the sensor probe 120 to be used to pierce the skin during a first period of time and subsequently to become less rigid or to change some other property according to an application. In some examples, the sensor probe 120 could include a material configured to initially have a high rigidity, to allow for piercing of skin, and to soften when the sensor probe penetrates the skin for a period of time. For example, the sensor probe 120 could include a piece of poly-2-hydroxyethyl methacrylate (poly-HEMA) or some other hydrogel configured to soften by absorbing water (e.g., from interstitial fluid) once the sensor probe 120 has penetrated the skin. In another example, the sensor probe 120 could include a stiff material that is configured to dissolve into and/or be absorbed by the skin (e.g., polylactic acid (PLA)).

Additionally or alternatively, the sensor probe 120 could be inserted into skin by another device that is configured to pierce the skin, or into an incision into the skin formed by another device. For example, the sensor probe 120 could be configured to be mounted within the channel of a half-needle of a device (e.g., a device configured to insert the sensor probe 120 into skin and/or to mount the flexible substrate 110 to a skin surface) such that the half-needle could pierce the skin and subsequently be retracted, leaving the sensor probe 120 in place penetrating the skin.

Note that the depiction of a body-mountable sensor platform 100 having a single sensor probe 120 on a distal end of which a single analyte sensor 125 is disposed and having an optical sensor 127 disposed on a bottom surface 150 of a flexible substrate 110 is intended as a non-limiting, illustrative example. A particular body-mountable sensing platform could include additional sensors disposed at different locations of the sensing platform (e.g., particular locations on a sensor probe). For example, a particular sensor probe of a body-mountable sensor platform could include a plurality of sensors disposed along the length of the particular sensor probe to allow for detection of some property of skin (e.g., a concentration of an analyte within the skin) at a variety of depths within the skin. A body-mountable sensor platform could include more than one sensor probe and such sensor probes could have respective widths, lengths, thicknesses, sensors, sensor locations, or other properties. Further, a body-mountable sensing platform could include sensors that are not disposed at a distal end or other locations on a sensor probe. For example, one or more sensors could be disposed on a flexible substrate (e.g., optical sensor 127 disposed on the bottom surface 150 of the flexible substrate 110) or other element(s) of such a body-mountable sensing platform.

The sensing platform 100 can be configured to operate using a very low amount of power, e.g., to allow the device to operate to measure a physiological property and to record, indicate, and/or transmit information about the measured physiological property over a protracted period of time, e.g., many hours, days, or weeks. This could include operating the display 160 to provide indications intermittently (e.g., in response to received user inputs) and/or the display 160 being configured to operate using very low power levels (e.g., the display 160 could be an electronic ink display or could otherwise provide indications by intermittently controlling the location, orientation, or other properties of the disposition of charged pigment particles within the display 160).

Additionally or alternatively, operating the sensing platform 100 using a very low amount of power could include operating the sensing platform, during a first period of time, to generate a plurality of digital codes (e.g., using an analog-to-digital converter (ADC) coupled to the output of a sensor configured to detect the physiological property) related to values of the physiological property of interest at respective different points in time (i.e., the generated codes represent samples of the physiological property over time) and to record the generated codes. The sensing platform 100 could then operate, during a second period of time, to determine values of the physiological property over time based on the recorded digital codes and calibration data obtained by (e.g., manually input into, received wirelessly, programmed into during manufacture, determined by a controller of) the body-mountable device. This conversion could be performed in response to a request (e.g., received from a user via a user interface, received from an external system via an antenna), in response to accessing a power source (e.g., radio frequency energy received wirelessly using an antenna of the body-mountable device), or according to some other factors or methods.

Such operation to determine values of a physiological property based on digital codes could require more power and/or energy than the operation of the body-mountable device during the first period of time (e.g., to generate and record digital codes relating to the property of interest). Such operation could be performed in response to a request received by the body-mountable device. For example, a user could operate a user interface (e.g., a touch sensor, a button, a capacitive touchscreen) to request an indication of the value of the physiological property, and in response the body-mountable device could determine a value of the physiological property based on the most recently generated and recorded digital code and the calibration data. The sensing platform 100 could further provide an indication related to the determined value (e.g., could present a numerical indication of the determined value using the display 160). In another example, the body-mountable device could receive a request (e.g., by receiving information wirelessly using an antenna) for values of the physiological property from an external system and could responsively determine one or more values of the physiological property based on corresponding one or more recorded digital codes and the calibration data. The body-mountable device could further transmit the determined values to the external system (e.g., wirelessly, using the antenna). Additionally or alternatively, the body-mountable device could transmit one or more of the recorded digital codes without converting them into determined values of the physiological property. In some examples, the body-mountable device could determine one or more values of the physiological property in response to receiving sufficient radio frequency energy (e.g., using a loop antenna or otherwise configured antenna) to do so.

The display of a body-mountable sensing platform as described herein (e.g., 160 of sensing platform 100) could be configured and/or fabricated in a variety of ways. In some examples, such a display could be composed of a number of layers of components, e.g., layers of components and/or material that are adhered to each other (e.g., by a layer of adhesive) or otherwise stacked to provide functions of a display. In some examples, a display could include a flexible substrate on which a plurality of electrodes of the display are disposed (e.g., each electrode could correspond to a segment of a portion of the display that is configured as a multi-segment display). A layer of display medium (e.g., a layer of liquid crystal, a layer of charged pigment particles disposed in a carrier fluid and/or carrier medium) could be disposed on the electrodes and the flexible substrate, and one or more transparent conductors (e.g., electrode(s)) could be disposed on the layer of display medium opposite the flexible substrate and electrodes disposed thereon. One or more further elements could be formed on or around such a display, e.g., one or more protective layers could be formed and/or disposed on or around the display to provide mechanical protection to the display, to prevent moisture or other environmental contaminants from interfering with the operation of the display, or to provide some other functionality. Methods for assembling and/or fabricating such a display could be performed as part of a roll-to-roll process.

Figure 2:
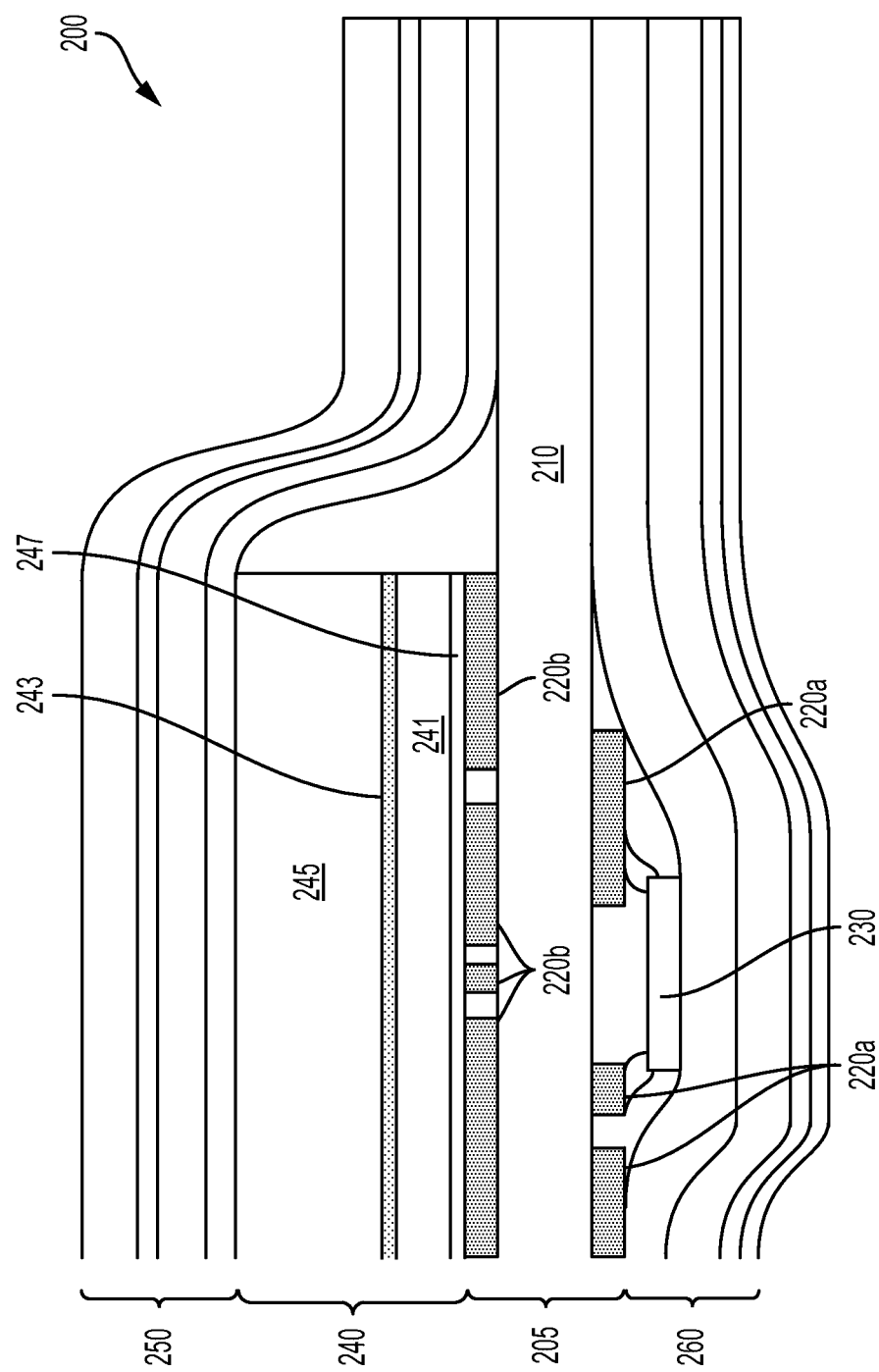
FIG. 2 is a cross-sectional view of elements of an example body-mountable device.

An example of a body-mountable device 200 including a display as described herein is shown, in cross-section, in FIG. 2. Components and/or elements of the device 200 are divided, for means of illustration, into four layers 205, 240, 250, 260. The first layer 205 includes a flexible substrate 210 and components formed and/or disposed thereon. A display layer 240 includes elements of a display of the device 200. A front sealant layer 250 and a rear sealant layer 260 are provided to provide mechanical and/or environmental protection to the other elements of the device 200 (e.g., to prevent moisture from the environment of the device 200 from affecting the operation of elements of the device 200).

First 220*a* and second 220*b* traces are disposed on respective first and second sides of the flexible substrate 210. The traces provide electrical connections for electronics of the device 200 (illustrated as an integrated circuit 230 electrically connected to the first traces 220*a*), e.g., to connect the electronic components to each other, to connect the electronics to sensors of the device 200. The second traces 220*b* also provide electrodes for the display, e.g., a plurality of electrodes corresponding to corresponding segments of a multi-segment numerical, trend-indicating, or otherwise configured display. The traces on the first 220*a* and second 220*b* sides of the flexible substrate 210 could be electrically connected by vias that pass through the flexible substrate 210 (e.g., through holes formed in the flexible substrate 210) or by some other means. In some examples, the traces 220*a*, 220*b* could provide antennas (e.g., loop antennas), electrodes of electrochemical sensors, electrodes of electrophysiological sensors (e.g., Galvanic skin response sensors, electromyogram sensors, skin conductivity sensors, electrocardiogram sensors), electrodes or other elements of a user input component (e.g., electrodes of a skin conductance sensor, electrodes of a capacitive touch sensor), electrodes of electrohaptic stimulators, contacts for electrically connecting to some other system(s) (e.g., charging contacts), or some other elements or functionality.

As described elsewhere herein, the flexible substrate 210 and traces 220*a*, 220*b* formed thereon can be composed of a variety of materials and formed by a variety of processes. For example, the flexible substrate 210 could be composed of polyimide, polyethylene terephthalate, or some other flexible polymeric or other material. The composition of the flexible substrate 210 could be chosen to allow for the formation and/or disposition of traces 220*a*, 220*b* on the flexible substrate 210. For example, the flexible substrate 210 could be composed of polyimide, polyethylene terephthalate, or some other polymeric and/or metallic material(s) such that metal contacts, electrodes, interconnects, and other features of the traces 220*a*, 220*b* can be patterned directly on the surface of the flexible substrate 210 (e.g., by sputtering, CVD, or some other deposition process) and/or on a coating or layer formed on one or more surfaces of the flexible substrate 210.

The display layer 240 includes a display medium 241 and a transparent conductive layer 243. The transparent conductive layer 243 is disposed on a polymer substrate layer 245. The display layer 240 further includes a display adhesive layer 247 configured to adhere the display layer 240 to the flexible substrate 210 and electrodes formed thereon (e.g., electrodes formed in the second traces 220*b*) such that the display medium 241 is located between the transparent conductive layer 243 and the electrodes formed on the flexible substrate 210. The display medium 241 is configured to have an optical property (e.g., a color, a reflectivity, a brightness, a luminous intensity) related to a voltage and/or current applied to the display medium 241 by the transparent conductive layer 243 and one or more electrodes formed in the second traces 220*b*.

The transparent conductive layer 243 could be composed of a variety of transparent conductive materials, e.g., the transparent conductive layer 243 could include indium tin oxide, a plurality of carbon nanotubes, a plurality of silver nanowires, or some other material(s) that are substantially transparent and that are conductive (e.g., that can conduct sufficient electrical current to allow a specified amount of voltage and/or current to be applied to regions of the display medium 241 to control the color, reflectivity, emissivity or other optical properties of the regions of the display medium 241 in order to provide indications using the display medium 241). The polymer substrate layer 245 is composed of a polymer material configured to be flexible (e.g., to allow the device 200 as a whole to conform to a skin or other tissue surface and to deform in response to deformation of such surfaces) and to provide a protective and/or supportive substrate for the display medium 241, transparent conductive layer 243, and/or other element(s) of the device 200. For example, the polymer substrate layer 245 could be composed of polyethylene terephthalate or some other polymer material. The polymer substrate layer 245 and/or other components of the display layer 240 could have a thickness specified according to an application, e.g., the polymer substrate layer 245 and the transparent conductive layer 243 could have a combined thickness of approximately 190 microns.

The transparent conductive layer 243 could be formed and/or deposited on the polymer substrate layer 245 by a variety of methods, e.g., sputtering, chemical vapor deposition, physical vapor deposition, application as part of a liquid solution (e.g., by spin-coating the polymer substrate layer 245) followed by curing, polymerization, evaporation of a solute of the solution, or some other process to form the transparent conductive layer 243. In some examples, traces, electrodes, or other shapes or features could be formed in the transparent conductive layer 243, e.g., by photolithography or some other process. Alternatively, the transparent conductive layer 241 could be formed as a foil or sheet and applied to the polymer substrate layer 245 using an adhesive (e.g., a pressure-sensitive adhesive) or using some other means.

The display medium 241 could include a variety of materials and/or structures configured such that a voltage and/or current can be applied to regions of the display medium 241 (e.g., using the transparent conductive layer 241 and electrodes of the second traces 220*b*) to control a color, brightness, reflectivity, intensity of emitted light, or other optical properties of the regions of the display medium 241. In some examples, the display medium 241 could include materials and/or elements configured as organic light emitting diodes such that, when a current is applied to a region of the display medium 241, the region emits light. In some examples, the display medium 241 could include a liquid crystal having an orientation, liquid crystal phase or other properties that are controllable by applying an electric field to regions of the display medium 241 (e.g., by applying a voltage between the transparent conductive layer 241 and one or more electrodes of the second traces 220*b* corresponding to the regions of the display medium 241). In such examples, the device 200 could include polarization filters, liquid-crystal-aligning ridges, reflectors, or other features such that electrically controlling properties of the liquid crystal of the display medium 241 (e.g., by applying a voltage and/or electric field thereto) can result in control of a reflectivity, brightness, or other optical properties of the display medium 241 and/or elements associated therewith.

In some examples, the display medium 241 could include charged pigment particles whose location within the display layer 241, orientation relative to the display layer 241, or other properties are related to observed optical properties (e.g., color, brightness, contrast) of the display medium 241 and/or elements associated therewith. The charge of the charged pigment particles could allow the location, orientation, or other properties of the charged pigment particles to be electrically controlled (e.g., by applying a voltage between the transparent conductive layer 241 and one or more electrodes of the second traces 220*b*).

In some examples, the charged pigment particles could be dipolar (i.e., individually having first ends that are positively charged and second ends that are negatively charged) and could have first and second halves that are aligned with the dipole of the charged particles and that have respective first and second colorations (e.g., black and white colorations, respectively). Application of an electric field to a region of the display medium 241 could control an orientation of the charged pigment particles in the region (e.g., by applying an electric torque to the charged particles) thus controlling the color of the region of the display medium 241 by controlling which coloration of the charged particles is directed toward a user (i.e., toward an external surface of the device 200).

In some examples, the charged pigment particles could have a first coloration (e.g., white) and could be disposed in a substantially opaque carrier fluid, gel, or other medium of the display medium 241 that has a second coloration (e.g., black). Application of an electric field to a region of the display medium 241 could control a location of the charged pigment particles in the region (e.g., by applying an electric force to the charged particles) thus controlling the color of the region of the display medium 241 by controlling the disposition of the charged pigment particles within the region. For example, regions of the display medium 241 wherein the charged pigment particles are disposed proximate the transparent conductive layer 243 could have a user-visible coloration similar to the coloration of the charged pigment particles (e.g., white) while regions of the display medium 241 wherein the charged pigment particles are disposed deeper within the display 160 could have a user-visible coloration similar to the coloration of the carrier fluid (e.g., black).

Application of a voltage to control the location and/or orientation of charged pigment particles in the display medium 241 could include applying a specified voltage between the transparent conductive layer 243 and one or more electrodes or other elements of the second traces 220b. In some examples, the specified voltage could have a magnitude related to a characteristic time of operation of the display medium 241, e.g., a characteristic time related to a rate of change of a color, reflectivity, or other optical property of regions of the display medium 241. In some examples, a greater specified voltage applied to transparent conductive layer 243 and one or more electrodes or other elements of the second traces 220b could be related to a decreased time to change a color or other optical property of the display medium (e.g., related to an increased rate at which the location and/or orientation of the charged pigment particles is changed). In some examples, the specified voltage could be a lower voltage, e.g., to reduce an amount of energy used to provide an indication. In some examples, this could include applying a voltage between the transparent conductive layer 243 and one or more electrodes or other elements of the second traces 220b that is between approximately 1 volt and approximately 2 volts. For example, the device 200 could include a flexible, single-layer battery (e.g., as illustrated in FIG. 1B) that provides a lower voltage (e.g., a flexible zinc battery that provides between approximately 0.8 volts and approximately 0.9 volts) and the applied voltage could be approximately equal to the voltage output of such a battery. Additionally or alternatively, the output of such a battery could be increased (e.g., via a boost circuit, via a capacitive voltage multiplier) and applied to the display medium 241. For example, a voltage between approximately 4 volts and approximately 10 volts could be applied to the display medium 241. Such a voltage could be produced by a battery (e.g., by a single cell of a battery or by multiple cells of a battery connected in series), by a boost converter, voltage multiplier, or other circuitry connected to a lower voltage source, or by some other means.

Charged pigment particles and carrier fluids or other media containing such could be disposed as part of the display medium 241 in a variety of ways. In some examples, the charged pigment particles and carrier fluids or other media could be disposed within a plurality of hollow microcapsules, e.g., hollow spheres of polyethylene terephthalate or some other polymer or other material. Such microcapsules could have a specified diameter, e.g., approximately 30 microns. The microcapsules could be disposed within the display medium 241 in a single layer or multiple layers (e.g., the display medium 241 could include a single layer of approximately 30 micron microcapsules such that the display medium 241 has a thickness of approximately 30 microns). The microcapsules could be bound within the display medium 241 and/or bound together to form the display medium 241 using an adhesive, e.g., a thermoplastic polyurethane.

The display medium 241, transparent conductive layer 243, and polymer substrate layer 245 could be attached to the flexible substrate 210 and/or second traces 220b by a layer of adhesive 247. The layer of adhesive could be a pressure sensitive adhesive, a thermoplastic adhesive, or some other adhesive. Further, the layer of adhesive 247 could be coextensive with an adhesive or other binding agent used to form the display medium 241. For example, the layer of adhesive 247 could be part of an amount of thermoplastic polyurethane used to bind a plurality of charged-pigment-particle-containing microcapsules together to form the display medium 241.

The first layer 205 and display layer 240 are enclosed by first 250 and second 260 sealant layers. The sealant layers 250, 260 could be configured to prevent moisture or other substances from the environment of the device 200 from interfering with the operation of the device 200, e.g., to prevent moisture from entering and/or contacting the display layer 241, the traces 220a, 220b, electronics (e.g., 230), transparent conductive layer 243, or other elements of the device. The first sealant layer 250 can be wholly or partially composed of substantially transparent materials to provide for visibility of the display medium (e.g., for indications provided by operation of the display medium 241 and/or other elements of the device 200 to be viewable by a user).

The sealant layers could be composed of multiple layers of material (as illustrated in FIG. 2) according to an application. In some examples, the first sealant layer could include a moisture barrier layer composed of Aclar® barrier film or some other transparent moisture barrier material; the first sealant layer could further include an outer layer disposed on the transparent moisture barrier material to protect the transparent moisture barrier material from scratches, ultraviolet radiation, or other sources of damage (e.g., the outer layer could be a layer of UV-stabilized polyethylene terephthalate). In some examples, the second sealant layer could include a moisture barrier layer composed of aluminum foil or some other opaque or transparent moisture barrier material. Different layers of each of the sealant layers could be joined by adhesives or by some other means to each other and/or to the first layer 205 and/or display layer 240. Such adhesives could be thermoplastic and/or elastomeric adhesives (e.g., a thermoplastic ethylene-vinyl acetate), pressure sensitive adhesives, or some other adhesives.

The device 200 could include additional or alternative elements to those illustrated in FIG. 2. For example, the device 200 could include an encapsulating layer (e.g., a sealant and/or adhesive layer, a layer configured to enable adhesion of the illustrated elements of the device 200 to some other elements) formed around the illustrated elements of the device 200, e.g., around the sealant layers 250, 260. Such an encapsulating layer could be formed of a silicone or of some other flexible material, e.g., to provide a further and/or alternative moisture barrier (e.g., a barrier against ingress of moisture along the edge of the device 200) and/or to provide some other functionality. Such an encapsulating layer could be formed by chemical vapor deposition, physical vapor deposition, spraying following by curing, drying, and/or polymerization, injection molding (e.g., placing the illustrated elements of the device 200 in a mold and adding uncured silicone or other materials to the mold, surrounding the illustrated elements of the device 200), or by some other method.

Separation of elements of the device 200 into layers (e.g., into the elements of the first layer 205 and the elements of the display layer 240) could allow for different fabrication processes to be used to form each of the layers separately, e.g., processes that could cause damage to elements of the device 200, followed by assembly of the different layers. For example, electrically connecting electronics (e.g., 230) to the first and/or second traces 220a, 200b could require high temperatures (e.g., temperatures sufficient to cause reflow of a metallic solder and/or a flux) that are high enough to cause damage to elements of the display layer, e.g., to burn and/or oxidize a carrier fluid and/or charged pigment particles of the display medium 241, to melt a binding agent of the display medium 241, and/or to melt the flexible polymer layer 245. In such examples, the high-temperature process could be performed to electrically connect the electronics to the traces 220a, 200b prior to adhering the display layer 240 to the flexible substrate 210 and second traces 200b. In some examples, this could include removably mounting the flexible substrate 210 and elements disposed thereon (e.g., traces 220a, 200b, electronics 230) in a jig formed to match the shape of the flexible substrate 210 and elements disposed thereon such that a surface to which the display layer 240 is to be adhered remains substantially flat. That is, such a jig could be formed to have a shape corresponding to the shape of a bottom surface of the flexible substrate 210 and elements disposed thereon (e.g., a shape that includes one or more depressions corresponding to the size, shape, and location of integrated circuits disposed on the flexible substrate 210).

A variety of sensor probes configured to penetrate skin, and devices (e.g., body-mountable sensing platforms) including such sensor probes, are described herein. Such sensor probes could be configured and/or operated to penetrate skin through a pre-existing cut, puncture, incision, or other entry through the surface of the skin into tissue (e.g., dermal tissue, subcutaneous tissue) containing an analyte-containing fluid of interest (e.g., interstitial fluid). Such a pre-existing entry could be formed for the purpose of inserting the sensor probe by a lancet, needle, or other instrument configured to pierce the skin. Additionally or alternatively, the sensor probe and/or some other element of a body-mountable sensing platform could be configured to pierce the skin, e.g., by including rigid elements, by including a sharpened end, or by being configured in some other way to allow piercing of the skin. In some examples, the sensor probe (and body-mountable sensing platform, in embodiments wherein the sensor probe is an element of such a sensing platform) could be removably mounted to an insertion device configured to pierce the skin in combination with the sensor probe and to retract leaving the sensor probe in place (i.e., penetrating the skin).

Figure 3B:
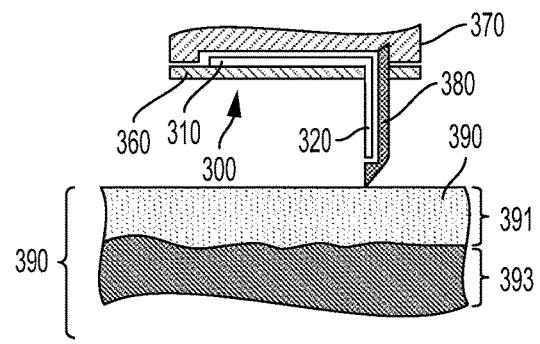
FIG. 3B is a cross-sectional view of the body-mountable device and insertion device of FIG. 3A, positioned proximate to skin of a living body.
Figure 3A:
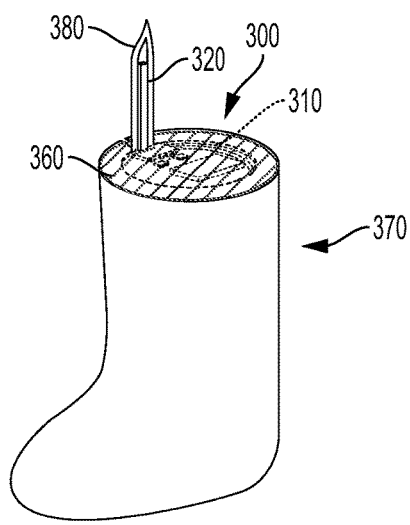
FIG. 3A is an aspect view of an example body-mountable device removably mounted to an example insertion device.

FIG. 3A illustrates an example body-mountable sensing platform 300 removably mounted to an example insertion device 370. The body-mountable sensing platform 300 includes a flexible substrate 310, a sensor probe 320 attached to the flexible substrate 310, and an adhesive layer 360 configured to adhere the flexible substrate 310 to a skin surface. The sensor probe 320 is configured to penetrate the skin and includes a sensor (not shown) disposed on the sensor probe 320 and configured to detect a property of the skin and/or to otherwise interact with tissues beneath and/or within the skin. For example, the sensor could be configured to detect an analyte (e.g., to measure a concentration of glucose) in a fluid within the skin (e.g., in interstitial fluid) when the sensor probe 320 penetrates the skin. The sensor probe 320 is coupled to a needle 380 of the insertion device 370. The needle 380 is a half-needle; that is, the needle 380 includes a channel along the length of the needle 380 in which the sensor probe 320 is disposed. The needle 380 is configured to pierce skin such that the needle 380 and the coupled sensor probe 320 penetrate the skin. That is, the needle is sufficiently rigid and/or has an end that is sufficiently sharp that force can be applied to the insertion device 370 such that the needle 380 pierces the skin. The insertion device 370 can then be moved away from the skin, retracting the needle 380 while the sensor probe 320 remains inserted in (i.e., penetrating) the skin and the flexible substrate 310 remains mounted on the skin surface.

Figure 3C:
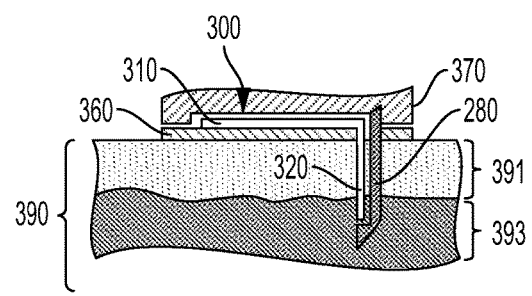
FIG. 3C is a cross-sectional view of the body-mountable device, insertion device, and skin of a living body of FIG. 3B, showing the body-mountable device and insertion device penetrating the skin.
Figure 3D:
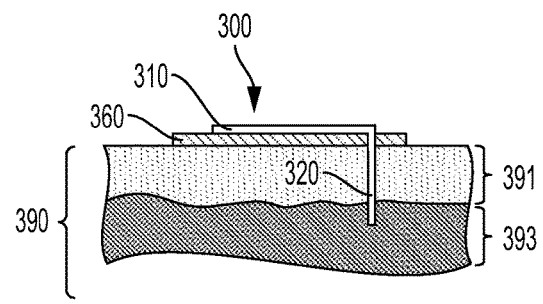
FIG. 3D is a cross-sectional view of the body-mountable device, insertion device, and skin of a living body of FIG. 3B, showing the body-mountable device penetrating the skin and the insertion device retracted from the skin.

FIGS. 3B-3D show, in cross-section, the process of using the insertion device 370 to pierce skin 390. The skin 390 includes an epidermal layer 391 and a dermal layer 393. FIG. 3B shows the body-mountable sensing platform 300 removably mounted to the insertion device 370 such that the sensor probe 320 of the sensing platform 300 is coupled to the needle 380 of the insertion device (that is, in this example, that the sensor probe 320 is disposed within a channel of the needle 380). As shown in FIG. 3B, the insertion device 370 and sensing platform 300 removably mounted thereto are disposed proximate the skin 390, but have not yet pierced and/or penetrated the skin 390.

FIG. 3C shows the insertion device 370 and sensing platform 300 after the needle 380 (and sensor probe 320 coupled thereto) has been inserted into the skin 390 (i.e., the needle 380 has pierced the skin). Further, the flexible substrate 310 has been mounted, via the adhesive action of the adhesive layer 360, to the skin 390 surface. The sensor probe 320 penetrates the skin 390 such that the distal end of the sensor probe 320 is located in the dermal layer 393 of the skin 390 (e.g., such that a sensor disposed on the end of the sensor probe 320 could detect an analyte in interstitial or other fluids present in the dermal layer 393). FIG. 3D shows the sensing platform 300 after the needle 380 of the insertion device 370 has been retracted. The sensor probe 320 continues to penetrate the skin 390 such that the distal end of the sensor probe 320 is located in the dermal layer 393 of the skin 390.

Note that the illustrated insertion device 370 and sensing platform 300 and use thereof to pierce and/or penetrate the skin 390, are intended as non-limiting illustrative examples of such devices and methods. An insertion device 370 and/or sensing platform 300 could have different shapes, include different components and/or elements, be configured different, and/or differ in some other way as will be clear to one of skill in the art. For example, the insertion device could consist of a disk to which a half-needle or other penetrating means are attached and to which a body-mountable sensing platform could be removably mounted. In some examples, the insertion device 370 could be configured to provide some additional functionality, e.g., could be configured to receive communications from the sensing platform (e.g., to receive information related to the detected analyte), to recharge a sensing platform, to activate a sensing platform, or to provide some other functionality. In some examples, an insertion device could include a driving mechanism (e.g., a spring-loaded mechanism, a servomechanism including one or more solenoids, motors, or other electromechanical actuators) configured to drive a needle (and sensor probe coupled thereto) into skin (e.g., to a specified depth within the skin, at a sufficiently high speed to minimize user discomfort). In some examples, the needle 380 could be retractable into the insertion device 370 for safety.

Note that the mounting of body-mountable sensing platforms to skin surfaces of living bodies, and in some examples the penetration of such skin by sensor probes of sensing platforms, are intended as non-limiting illustrative examples of devices and methods described herein. Such devices and systems could be used to detect other properties of a body and/or of the environment of the devices and systems in some other way. This could include detecting analytes in or other properties of other tissues by penetrating such other tissues with sensor probes and/or mounting flexible substrates to surfaces of such tissues. For example, sensor probes, flexible substrates, and/or sensing platforms as described herein could be used to detect an analyte within a mucosal epithelium (e.g., within the mucosa of a mouth, nose, or other mucosa of a living body). Additionally or alternatively, sensor probes, flexible substrates, and/or sensing platforms as described herein could be used to detect analytes in a variety of fluids without penetrating tissues (e.g., to detect an analyte in a tissue present in a volume of a living body, e.g., to detect an analyte in peritoneal fluid by disposing a sensing-platform as described herein within the peritoneal cavity of a living body). Further, systems and devices as described herein could be used to detect properties of an animal and/or plant body, and/or to detect properties of a natural environment (e.g., a stream, a lake) and/or an artificial environment (e.g., a pharmaceutical process, a water treatment process, a food processing process).

A sensor disposed at a distal end of a sensor probe or at some other location of a body-mountable sensing platform as described herein could include a variety of components and/or substances configured in a variety of ways. In some examples, such sensors could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or otherwise selectively interact with an analyte of interest. Such an analyte-sensitive substance could be disposed on a surface of a sensing platform (e.g., on a metal surface of an electrode, on a surface of an optical fiber, on some other surface of a sensor probe and/or flexible substrate) and/or within a polymer, gel, or other layer that is permeable to the analyte and that is disposed on such a surface.

In some examples, an analyte-selective substance could be disposed on a surface of a sensing platform (e.g., on an electrode surface) by crosslinking the substance on the surface (e.g., using glutaraldehyde to crosslink the analyte-sensitive substance). In some examples, an analyte-selective substance can be disposed within a polymer layer formed on a surface of a sensing platform. Such a polymer layer can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer that contains the analyte-selective substance is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, in increase a degree of crosslinking of the hydrogel, or to specify one or more other properties of the hydrogel. For example, such a hydrogel could additionally include di(ethylene glycol) dimethacrylate units.

In some examples, the sensor of a sensing platform can include two or more electrodes configured to detect or measure the analyte electrochemically. The two or more electrodes could include a working electrode selectively sensitive to the analyte and a reference electrode. In some examples, exposing the sensor to a target fluid (e.g., interstitial fluid) causes a potentiometric voltage to develop between the working electrode and the reference electrode that can indicate the concentration of the analyte near the working electrode. Additionally or alternatively, a specified voltage could be applied between the reference electrode and the working electrode and an amount of current that responsively flows through the working electrode could be related to the concentration of the analyte near the working electrode and/or the rate at which the analyte diffuses to the working electrode (e.g., through a hydrogel layer containing an analyte-selective substance and/or through a hydrogel layer disposed to protect the working electrode and/or other components of the sensor).

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor platform could include a light emitter and/or a light detector configured to illuminate and to receive light emitted from the analyte-sensitive substance, respectively, in order to determine the optical property of the substance that is related to the analyte. In some examples, a sensor probe of the sensing platform could include an optical fiber and the analyte-selective substance could be disposed on a distal end of such an optical fiber. In such examples, a light emitter and/or a light detector could be disposed at a proximal end of the optical fiber, such that the light emitter and light detector illuminate and received light from the analyte-sensitive substance via the optical fiber. In such examples, the light emitter and/or light detector could be disposed on a flexible substrate of the sensor platform (e.g., as part of electronics disposed on the flexible substrate).

In some examples, a polymer, gel, or other layer that is permeable to the analyte could be disposed over to one or more components of the sensor (e.g., over a working electrode, over a layer containing and/or composed of an analyte-selective substance) and/or other elements of a sensing platform to protect the elements of the sensing platform or according to some other application. In some examples, a permeability, thickness, or other properties of such an analyte-permeable layer (and/or of a similar layer containing an analyte-selective substance) could be specified to control a rate of diffusion of the analyte from interstitial fluid to a sensor (e.g., to a metal electrode surface of the sensor) or to some other element of the sensing platform (e.g., to an analyte-selective substance disposed proximate to an electrode, optical fiber, or some other element of the sensing platform). In some examples, a protective or other polymer layer could be a hydrogel, e.g., a hydrogel that includes units of 2-hydroxyethyl methacrylate and/or units of di(ethylene glycol) dimethacrylate.

In some examples, a sensor of a body-mountable sensing platform could be configured to detect an optical property of a tissue and/or of a body to which the sensing platform is mounted. This could include detecting a reflectance, absorbance, fluorescence intensity, fluorescence lifetime, or some other optical properties of tissue. Such detection could include emitting light toward and/or detecting light emitted from a tissue in one or more bands of wavelengths and/or within a plurality of such bands of wavelengths. For example, an optical sensor could be configured to detect a reflectance spectrum, an absorbance spectrum, a fluorescence spectrum, an excitation spectrum, an emission spectrum, or some other spectral information or spectrum relating to optical properties of a tissue. Such an optical sensor could include one or more photodetectors, photodiodes, phototransistors, or other light-detecting elements configured to detect light within one or more bands of wavelengths, within a specified range of polarizations, or having some other specified properties. Such an optical sensor could include one or more LEDs, lasers, or other light-emitting elements configured to emit light within one or more ranges of wavelengths, having a specified polarization, a specified coherence length, a specified angle relative to skin and/or one or more photodetectors, or some other specified property.

Such an optical sensor could detect one or more optical properties related to the presence and/or amount of a substance (e.g., a concentration of hemoglobin in blood, a volume of blood in a portion of skin), a property of a substance (e.g., an oxygenation state of hemoglobin in blood), or some other properties of skin. Such detected properties could be used to determine one or more properties of the skin to which the sensing platform is mounted and/or of a body comprising the skin. For example, an optical sensor could be configured and/or operated to detect an oxygenation of blood in the skin, a timing and/or frequency of pulses of blood in the skin and/or of heartbeats of the heart of the body comprising the skin, a degree of perfusion of the skin, or some other properties.

A body-mountable sensor platform could include additional or alternative sensors. Such sensors could include temperature sensors, accelerometers, gyroscopes, magnetometers, barometric pressure sensors, magnetic field sensors, electric field sensors, electromagnetic field sensors, or other types of sensors. Such sensors could be configured and/or operated to detect properties of skin to which the sensing platform is mounted and/or to detect properties of the environment of the sensing platform. Such sensors could include two or more electrodes configured to detect an electrical potential between and/or an electrical current through the two or more sensors. Such sensors could be configured and/or operated to detect a galvanic skin conductance, a galvanic skin potential, an electromyogram, an electrocardiogram, or some other electrophysiological property of skin to which the sensing platform is mounted and/or of a body comprising the skin. A body-mountable sensing platform could include additional or alternative sensors and/or combinations thereof.

The particular body-mountable sensing platforms, displays, input components, user interfaces, sensors, and configurations and operations thereof illustrated herein (e.g., as body-mountable sensing platforms 100, 200, 300, 400) are intended as non-limiting examples. Differently-configured sensing platforms (e.g., having differently-shaped and/or sized flexible substrates or other components), displays, input components, or other properties of the configuration and operation of body-mountable sensing platforms are anticipated, as will be clear to one of skill in the art.

III. EXAMPLE ELECTRONICS OF A FLEXIBLE BIOSENSOR PLATFORM

Figure 4:
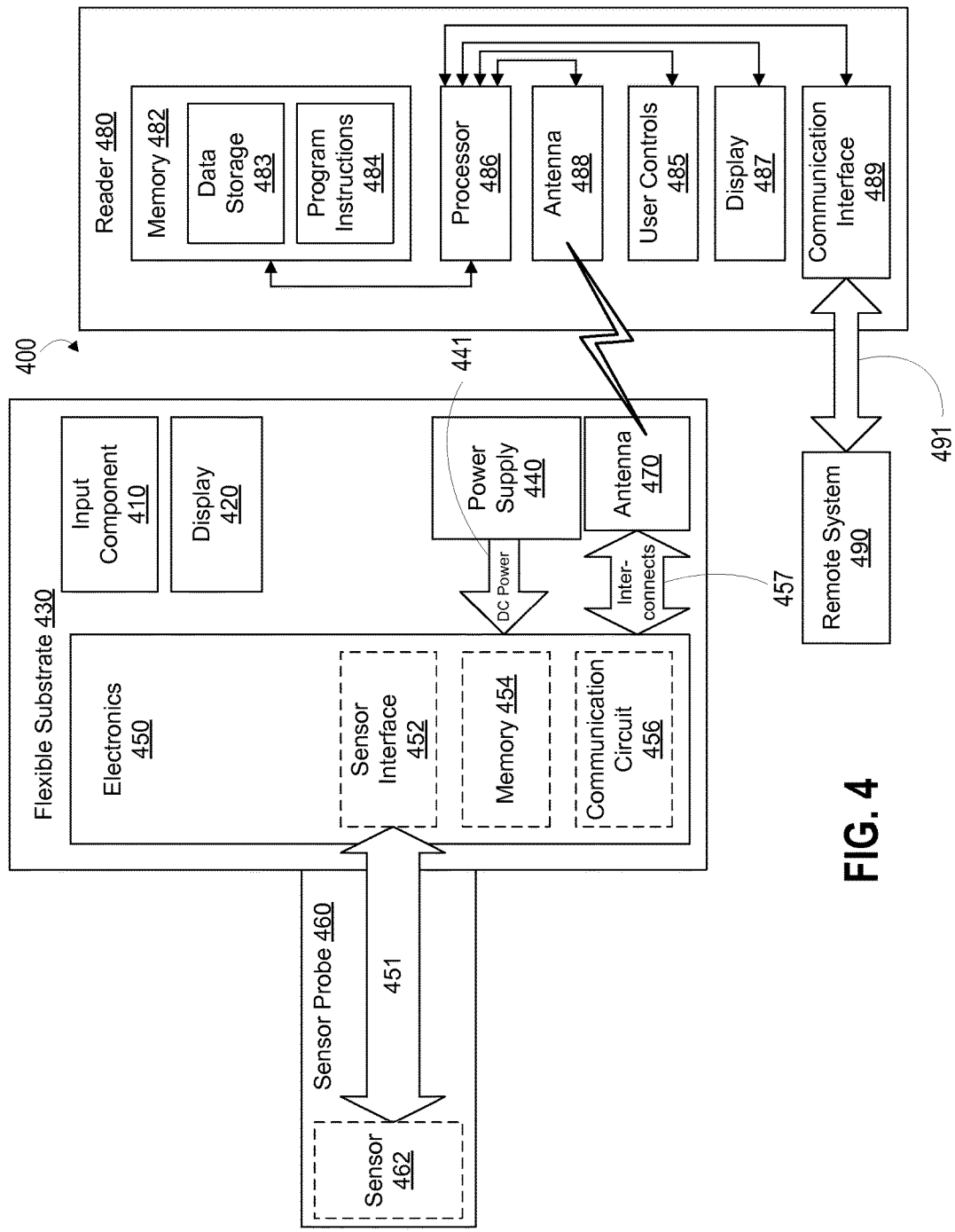
FIG. 4 is a block diagram of an example system that includes a body-mountable device in wireless communication with an external reader.

FIG. 4 is a block diagram of a system that includes a body-mountable sensing platform 400 in wireless communication with an external reader 480. The sensing platform 400 includes a flexible substrate 430 that is made of a flexible polymeric or metallic material formed to be mounted to a skin surface. The flexible substrate 430 provides a mounting surface for a power supply 440, electronics 450, input component 410 and display 420 of a user interface, and a communication antenna 470. The power supply 440 supplies operating voltages to the electronics 450 and/or other elements of the sensing platform 400. The antenna 470 is operated by the electronics 450 to communicate information to and/or from the sensing platform 400. The antenna 470, the electronics 450, display 420, input component 410, and the power supply 440 can all be situated on the flexible substrate 430. Further, the sensing platform 400 includes a sensor probe 460 that is configured to penetrate skin or some other tissue. The sensor probe 460 has a first end connected to the flexible substrate 430 and a second end configured to penetrate the skin or other tissue such that a sensor 462 disposed on the sensor probe 460 is in contact with interstitial fluid or some other target fluid (e.g., blood, tears) on or within the skin or other tissue.

The flexible substrate 430 and/or elements of the sensing platform 400 disposed thereon can have a thickness, shape, composition, rigidity, compliance, elasticity, viscoelasticity, and/or other properties specified such that the flexible substrate 430 can be mounted to a skin surface of a living body and further such that such mounting minimally interferes with activities of the living body (e.g., motions of the living body). This could include the flexible substrate 430 being sufficiently flexible that mounting of the flexible substrate 430 to the skin surface causes a minimum of discomfort. The flexible substrate 430 could be composed of polyimide or some other flexible polymeric or other material. One or more surfaces of the flexible substrate 430 could be used as a platform for mounting components or elements of the antenna 470, the electronics 450, display 420, input component 410, and the power supply 440. Such components could include integrated circuit chips (e.g., via flip-chip mounting) and conductive materials (e.g., via deposition techniques) that form electrodes, antenna(e), and/or connections. The composition of the flexible substrate 430 could be specified such that metal contacts, traces, and interconnects can be patterned directly on the surface of the flexible substrate 430 (e.g., by sputtering, CVD, or some other deposition process) and/or on a coating or layer formed on one or more surfaces of the flexible substrate 430.

The sensing platform 400 could be sufficiently flexible that the flexible substrate 430 and components mounted thereto/dispose therein conform to the shape of the skin surface and changes in the shape of the skin surface. This could include elements disposed on/in the flexible substrate 430 being flexible. For example, elements (e.g., electronics 450, input components 410, displays 420) could include or be composed of flexible polymers, flexible metal films, traces, and/or electrodes (e.g., metal traces or electrodes formed on the flexible substrate 430, a thin layer of flexible transparent conductive material disposed proximate a flexible layer of display medium of the display 420), or other flexible materials and/or materials formed to be flexible (e.g., a rigid material formed to include a strain relief, to be thin or narrow, or otherwise formed such that an element composed of the rigid material is functionally flexible).

The electronics 450 disposed on the flexible substrate 430 could include a variety of devices. For example, the electronics 450 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 430. Further, antennas, electrodes, capacitors, resistors, or other components could be formed from such traces or other interconnects formed on the surface of the flexible substrate 430. The electronics 450 can include logic elements configured to operate the sensor 462 to detect a property (e.g., an analyte in a body), an antenna (e.g., a loop, dipole, or other type of antenna formed on the flexible substrate 430, or a chip antenna disposed on the flexible substrate 430) to wirelessly indicate information (e.g., concentration levels) about the detected analyte, an electrode of a capacitive touch sensor to receive an input, and/or to provide other functions. Electrical interconnects (e.g., traces), antennas, and/or conductive electrodes (e.g., for an electrochemical analyte sensor, etc.) can be formed from conductive materials patterned on the flexible substrate 430 by a process for precisely patterning such materials, such as deposition, lithography, etc. The conductive materials patterned on the flexible substrate 430 can be, for example, gold, platinum, palladium, titanium, carbon, aluminum, copper, silver, silver-chloride, conductors formed from noble materials, metals, combinations of these, etc.

The sensing platform 400 further includes a sensor probe 460 that is attached to the flexible substrate 430. The sensor probe 460 is an elongate element of the sensing platform 400 that is configured to penetrate a skin surface such that a sensor 462 located at a distal end of the sensor probe 460 is disposed within tissue (e.g., in contact with interstitial fluid, blood, or some other fluid of interest) when the sensor probe 460 is penetrating the skin. That is, the sensor probe 460 is configured to extend beneath the skin surface into an epidermal, dermal, or subcutaneous tissue of a body that includes the skin surface. The sensor probe 460 could be composed of a flexible material (e.g., polyimide) or a relatively inflexible material; further, a thickness, width, shape, or other properties of the sensor probe 460 could be specified to provide a degree of flexibility or inflexibility. In some examples, the sensor probe 460 could be formed from the same material as the flexible substrate 430; i.e., the sensor probe 460 could be an elongate portion of the flexible substrate 430 that extends from a portion of the flexible substrate 430 that is configured to be mounted to a skin surface and/or on which electronics 450 or other components are disposed. Alternatively, the sensor probe 460 could be attached to the flexible substrate 430. For example, the sensor probe 460 could include optical fiber(s), wire(s), elongate pieces of shaped silicon, patterned conductive traces, or other elements adhered, welded, bonded, or otherwise attached to the flexible substrate 430. Alternatively, such sensor probes could be used for other applications and/or in combination with components or devices other than a flexible substrate (e.g., 430) as described herein.

The substrate 430 includes one or more surfaces suitable for mounting the electronics 450 (including a sensor interface 452, a memory 454, and a communication circuit 456), the power supply 440, the input component 410, the display 420, and the antenna 470. The flexible substrate 430 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For example, the antenna 470 can be formed by depositing a pattern of gold or another conductive material on the flexible substrate 430. Similarly, interconnects 441, 451, 457 between the electronics 450 and the power supply 440, between the sensor interface 452 and the sensor 462, and between the communication circuit 456 and the antenna 470, and/or other interconnects between components of the device 400, can be formed by depositing suitable patterns of conductive materials on the substrate 430. A combination of microfabrication techniques including, without limitation, the use of photoresists, masks, deposition techniques and/or plating techniques can be employed to pattern materials on the substrate 430. The substrate 430 can be a material, such as polyimide, polyethylene terephthalate ("PET"), parylene, or another material sufficient to structurally support the circuitry and/or electronics.

The power supply 440 is configured to provide energy to power the electronics 450. For example, the power supply 440 could include a battery. Such a battery could be flexible, e.g., the battery could be a flexible lithium-ion battery or some other type of flexible battery. The battery could be flexible to allow the flexible substrate 430 to which the battery is mounted to flex in response to deformation and/or motion of a skin surface to which the flexible substrate 430 is mounted. Such flexibility could be provided to increase the comfort of a living body to which the sensing platform 400 is mounted and/or to minimally interfere with motions and/or activities of such a living body. A battery (or combination of batteries provided as part of the power supply 440) could have a capacity sufficient to power the device for a protracted period of time, e.g., 18 hours, a week, or some other protracted period of time of periodic operation of the sensor 462, antenna 470, and memory 454 to detect an analyte, to record information related to the analyte in the memory 454, and to wirelessly communicate such detected information to the external reader 480. For example, the battery could be a flexible battery with a capacity of more than approximately 60 microamp-hours and a thickness of less than approximately 0.5 millimeters.

In some examples, the power supply 440 could include a rechargeable battery and could further include some means for recharging such a battery. For example, the power supply 440 could include contacts disposed on a surface of the flexible substrate 430 and configured to receive electrical power from complimentary contacts of a charging device (e.g., the external reader 480). In another example, the sensing platform 400 could include a loop antenna (e.g., a loop antenna comprising conductive traces patterned on the flexible substrate 430) and the power supply 440 could be configured to use the loop antenna to receive RF energy from an external device (e.g., the external reader 480); in some examples, such an RF-energy-receiving antenna could be the same antenna as the antenna 470 used to communicate with external devices.

The display 420 could include OLED, LED, liquid crystal, electronic paper, or other components configured to emit a light, change a color, or otherwise visually indicate some information. In some examples, the display 420 could include one or more discrete light emitters (e.g., LEDs, OLEDs) configured to emit light to indicate some information (e.g., to indicate an alert, to indicate a battery status, to indicate some information related to a property detected by the sensor 462). A portion of the display 420 could be configured as a multi-segment numerical display (e.g., to have one or more seven-segment numerals configured to provide indications of numerical information, e.g., analyte concentrations measured using the sensor 462). Each segment of such a multi-segment numerical display could correspond to at least one respective electrode of the display 420 (e.g., an electrode formed on the flexible substrate 430). Additionally or alternatively, a portion of the display 420 could be configured as a multi-segment trend display. Such a multi-segment trend display of the display 420 could have several segments that that could be operated to indicate an increasing or decreasing trend, e.g., across multiple detected values of a physiological property detected by the sensor 462. The multi-segment trend display could be configured to indicate a trend by indicating an upward- or downward-pointing arrow, respectively. Each segment of the multi-segment trend display could correspond to at least one respective electrode of the display 420 (e.g., an electrode formed on the flexible substrate 430). The display 420 could be configured in some other way and/or operated to provide indications of and/or related to some other information.

In some examples, the display 420 could be configured and/or operated to consume very little power. For example, the sensing platform 400 could be powered by a low-capacity battery (e.g., a flexible, thin, single-cell zinc battery) of the power supply 440 and the display 420 could be configured and/or operated such that the battery can power the sensing platform 400 for an extended period of time, e.g., several days, two weeks, or some other period of time. In some examples, this could include operating the display 420 intermittently, e.g., only operating the display 420 to indicate information (e.g., measured analyte concentrations) during specified periods of time, e.g., in response to a user providing an input (e.g., a press or touch of a finger against the sensing platform 400 detected by a capacitive touch sensor or other element (s0 of the input component 410) the display 420 could be operated to provide such an indication for a specified period of time.

Further, the display 420 could be configured to operate using a low power budget. For example, the display 420 could be a liquid-crystal display, an electronic paper display, or some other display technology configured to provide a visual indication using little power. Such operation can use power only when changing an indication provided by the display 420, e.g., to change the location, orientation, or other properties of charged pigment particles within a display medium of the display 420 (e.g., by applying a voltage and/or current to regions or segments of the display 420). Such a provided indication could remain on the display 420 until some specified condition is met (e.g., until an updated indication is requested). Additionally or alternatively, the display 420 could be blanked (e.g., set to a single color/reflectivity or otherwise set to some default display state) after a specified period of time passes from a time when the display 420 is operated to provide an indication.

In a particular example, the display medium of the display 420 could include charged pigment particles disposed in a carrier fluid or other medium (e.g., a liquid polymer, a colored hydrocarbon oil). For example, the display 420 could be an electronic paper display. The location, orientation, and/or disposition of the charged pigment particles within the display medium can be controlled by applying electric fields to the display medium (e.g., by applying specified voltages between electrodes and/or transparent conductive layer(s) of the display 420) to control the color and/or reflectivity of segments or regions of the display. In some examples, the display medium could include a plurality of hollow beads (e.g., hollow beads composed of a polymer and having diameters of approximately 30 microns) within which such charged particles, carrier fluids, and other display elements could be disposed. In such examples, the plurality of hollow beads could be disposed in a layer (e.g., disposed within a layer of polymer configured to contain the beads) such that the display medium is flexible and further such that the display medium can be cut or otherwise modified to assume a specified shape without forming any termination or seal at the edge of any such cuts, e.g., to prevent a fluid of the display medium from leaking out of the display.

Further, the sensing platform 400 could include additional output components or other means for providing indications to a user. For example, the sensing platform 400 could include speakers, piezo elements, or acoustical elements or other means for generating sounds to indicate information (e.g., to beep, to generate a tone, to play a recorded and/or synthesized sound). The sensing platform 400 could include a vibrator, one or more electrodes configured to deliver an electro-haptic stimulus to skin, a heating element configured to heat skin, or some other haptic elements configured to deliver a haptic stimulus to a person.

The input component 410 is configured to receive inputs from a user (e.g., a user to whose body the device is mounted) to provide some application(s) of the sensing platform 400. Such user-interface elements (e.g., sensors, buttons) could be flexible and/or mounted to and/or formed on (e.g., flexible electrodes of a capacitive touch sensor and/or electro-haptic stimulator) the flexible substrate 430 of the sensing platform 400. In some examples, the input component 410 could provide means for changing or setting an operational state or operational parameter of the sensing platform 400 and/or for causing the performance of some function by the sensing platform 400.

For example, the input component 410 could provide means for a user to cause the sensing platform 400 to perform a measurement of a physiological property using the sensor 462, to set the sensing platform 400 into a sleep or other low-power state, to set a rate of operation of the sensor 462 to detect a physiological property, to operate the display 420 to provide some indication (e.g., to provide an indication related to data measured using the sensor 462), or to control some other aspect of operation or function of the sensing platform 400. In some examples, the input component 410 could provide means for inputting calibration or other data to the sensing platform 400, e.g., for inputting calibration data related to the operation of the sensor 462 to detect a physiological property. Additionally or alternatively, the input component 410 could provide means for inputting information about the state of a user of the sensing platform 400, e.g., to indicate a physical or mental state of the user, to indicate an activity of the user, to indicate that the user has eaten a meal or taken a drug, or to indicate some other information.

The input component 410 could be configured to receive inputs related to communication between the sensing platform 400 and an external system (e.g., reader 480). For example, the sensing platform 400 could be configured to communicate information related to a measurement made by the sensor 462 (e.g., using the communication circuit 456 and antenna 470) in response to a received input. The communicated information could include stored information (e.g., analyte concentration values detected using the sensor 462 at a plurality of past points in time and stored in the memory 454); additionally or alternatively, the communicated information could include information obtained using the sensor 462 in response to the received input. In some examples, the communicated information could include information related to an information link between the sensing platform 400 and the external system (e.g., reader 480). For example, the communicated information could include a request for further communication and/or a request for information about a communications protocol (e.g., the communicated information could include information related to linking the sensing platform 400 with the external system, e.g., related to performing a Bluetooth pairing between the sensing platform 400 and the external system). Further, the communicated information could include security information (e.g., cryptographic keys, passwords) related to securing further communication between the sensing platform 400 and the external system.

The input component 410 could be configured to receive a variety of inputs by detecting a variety of physical variables. The input component 410 could be configured to detect sound (e.g., voice commands), motions of the sensing platform 400 (e.g., a gesture that includes motion of the skin surface to which the sensing platform is mounted), contact between the sensing platform 400 and a finger or other portion of a user's body, the presence, location, motion, or other properties of a finger or other object proximate the input component 410, or some other inputs. For example, the input component 410 could be configured to detect a location, motion, pressure, gesture, or other information about objects (e.g., a finger or other body part) proximate the sensing platform 400. The input component 410 could include a capacitive touch sensor configured to detect a single touch, multiple touches, gestures, swipes, or other inputs. The input component 410 could include flexible components. In some examples, the input component 410 could include one or more elements in common with the display 420. For example, an electrode and/or transparent conductive layer of the display 420 could be used as an electrode of a capacitive touch sensor.

The sensor interface module 452 and connections 451 between the sensor interface module 452 and the sensor 462 could take a variety of forms according to the methods used to detect a physiological property (e.g., an analyte in interstitial fluid to which the sensor 462 is exposed). The sensor 462 can include an analyte-selective substance that selectively interacts with the analyte in a fluid (e.g., interstitial fluid in skin, sweat on the surface of the skin). The analyte-selective substance can include proteins, enzymes, reagents, ionophores, antibodies, fluorophores, nano-structured surfaces and/or structures, or other substances that selectively bind to, react with, change one or more properties in response to the presence of, or otherwise selectively interact with the analyte. The sensor 462 and sensor interface 452 can then detect the selective interaction between the analyte and the analyte-selective substance to detect a presence, concentration, or other properties of the analyte.

Such detection can include detecting the interaction between the analyte and the analyte-selective substance directly (e.g., by detecting a change in an optical property of the analyte-selective substance in response to interaction with the analyte, by detecting a change in electrical potentials at the sensor 462 due to accumulation of a charged analyte by the analyte-selective substance) or indirectly (e.g., by detecting a reaction product of the selective reaction of the analyte, e.g., by detecting hydrogen peroxide produced by oxidation of the analyte by the analyte-selective substance). Direct or indirect detection of the analyte could include electrochemical detection (i.e., the sensor could include two or more electrodes configured to electrochemically detect the analyte), optical detection (i.e., the sensor 462 and/or the sensor interface 452 could include a light emitter and/or light detector configured to detect an optical property of the analyte and/or the analyte-selective substance that is related to the presence, concentration, or some other property of the analyte), or some other detection means.

In some examples, the sensor 462 includes at least a reference electrode and a working electrode. The working electrode is selectively sensitive to an analyte of interest, for example, by having an analyte-selective substance localized proximate to the working electrode (e.g., by being disposed on a surface of the working electrode, by being disposed in an analyte-permeable polymer layer disposed on the working electrode). The sensor interface 452 is configured to operate the sensor 462 to electrochemically detect the analyte.

In some examples, the sensor 462 can be a potentiometric sensor. In such examples, a voltage can develop between the working and reference electrodes related to a concentration of analyte in a fluid to which the working electrode is exposed. Thus, the sensor interface 452 can measure a magnitude of the potentiometric voltage between the working electrode and the reference electrode to provide an indication of analyte concentration. In such embodiments, the sensor interface 452 can include a high-impedance voltmeter configured to measure the voltage difference between working and reference electrodes while substantially preventing the flow of current through the working and reference electrodes.

Additionally or alternatively, the sensor 462 can be an amperometric sensor. In such examples, the sensor interface 452 can apply a specified voltage between the reference electrode and the working electrode. The applied voltage can drive an electrochemical current through the working electrode that is related to the concentration of an analyte near the working electrode. Such an electrochemical current can be related to redox or other reactions of the analyte at the surface of the working electrode and/or could be related to redox or other reactions of reaction products of the analyte at the surface of the working electrode (e.g., reaction products produced by reaction of the analyte due to selective interaction with the analyte-selective substance). Thus, the sensor interface 452 can measure a magnitude of the amperometric current passing through the working electrode to provide an indication of analyte concentration. In such embodiments, the sensor interface 452 can include a specified voltage source (to provide the specified voltage between the reference electrode and the working electrode) and a current meter configured to measure the current passing through the working electrode due to the applied specified voltage. In some examples, the sensor 462 could additionally include a counter electrode through which a return current (i.e. a current having a magnitude substantially equal but opposite to the current passing through the working electrode) could pass, such that substantially no current passes through the reference electrode. Such an embodiment could allow for the reference electrode to provide a more stable voltage relative to the fluid to which the sensor 462 is exposed.

In some examples, the sensor 462 could include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. In some examples, such an analyte-selective substance could include a protein or other element configured to selectively bind to the analyte and to experience a conformation change in response to such binding. A fluorophore and a quencher could be attached to the protein such that the distance between the fluorophore and the quencher is related to whether the protein is bound to the analyte; as a result, the degree of fluorescence of the fluorophore could be related to whether the protein is bound to the analyte. Additionally or alternatively, a color, saturation, absorption spectrum, or some other optical property of a substance disposed at the end of the sensor probe could be related to the presence, concentration, or some other property of the analyte.

In such examples, the sensor interface 452 and/or the sensor 462 could include a light emitter and/or a light detector configured to illuminate and/or to receive light emitted from the analyte-sensitive substance, respectively, in order to determine the optical property of the substance that is related to the analyte. In some examples, the light emitter and/or light detector could be disposed as part of the sensor 462 (i.e., disposed on the sensor probe 460) and connected to the sensor interface 452 via conductive interconnects (e.g., the sensor interconnect 451 could include traces patterned or otherwise disposed on the sensor probe 460). Additionally or alternatively, the sensor probe 460 could include an optical fiber and the analyte-selective substance could be disposed on a distal end of such an optical fiber. In such examples, the light emitter and/or a light detector could be disposed at a proximal end of the optical fiber (e.g., on the flexible substrate 430 as part of the sensor interface 452), such that the light emitter and light detector illuminate and/or receive light from the analyte-sensitive substance via the optical fiber.

The memory 454 could include a variety of volatile and nonvolatile electronic storage elements configured to provide means for the sensing platform 400 to record and/or log detected information about the analyte (e.g., concentrations measured using the sensor 462 at a plurality of points in time) and/or other information detected by or input to (e.g., via the input component 410) the sensing platform 400. For example, the memory 454 could include one or more EEPROM memories, flash memories, NVRAM memories, DRAM memories, SRAM memories, flip-flops, or other information storage elements. The memory 454 could have an information storage capacity sufficient to record some specified period of detected information at some specified rate of detection; e.g., the memory 454 could have a capacity sufficient to record more than 18 hours, a week, or some other protracted period of time of detected information (e.g., concentrations of an analyte) when detected at a rate of approximately once per minute. Additionally or alternatively, the sensing platform 400 could be in communication with a memory that is external to the sensing platform 400 and that could be used as described above (e.g., to store physiological property measurement data, to store and/or access calibration or other configuration data of the sensing platform 400).

The electronics 450 include a communication circuit 456 for sending and/or receiving information via the antenna 470. The communication circuit 456 can optionally include one or more oscillators, mixers, frequency injectors, etc. to modulate and/or demodulate information on a carrier frequency to be transmitted and/or received by the antenna 470. In some examples, the sensing platform 400 is configured to indicate information (e.g., detected analyte concentrations using the probe sensor 462) by modulating an impedance of the antenna 470 in a manner that is perceivably by the external reader 480. For example, the communication circuit 456 can cause variations in the amplitude, phase, and/or frequency of backscatter radiation from the antenna 470, and such variations can be detected by the reader 480. Such wireless communication could be compatible with one or more existing backscatter wireless communications standards, e.g., RFID. Additionally or alternatively, the communication circuit 456 and antenna 470 could be configured to transmit wireless signals according to some other method, e.g., according to the Bluetooth (e.g., Bluetooth Low Energy), ZigBee, WiFi, LTE, and/or some other wireless communications standard or scheme. In some examples, such communications (e.g., data transmitted from the sensor platform 400, operational instructions transmitted to the sensor platform 400) could be cryptographically secured; that is, the wireless communications link could be encrypted.

The sensor interface 452 is connected to the sensor 462 via a sensor interconnect 451. In some examples, the sensor interconnect 451 could include a patterned conductive material (e.g., gold, platinum, palladium, titanium, copper, aluminum, silver, metals, combinations of these, etc.) to connect electrodes, light emitters, light detectors, or other components of the sensor 462 to a terminal on a microcontroller or other component(s) comprising the sensor interface 452. Similarly, the electronics 450 are connected to the antenna 470 via interconnects 457. Additionally or alternatively, the sensor interconnect 451 could include an optical fiber or other means for transmitting light between the sensor 462 and the sensor interface 452. For example, the sensor interface 452 could comprise a light emitter and/or light detector and the sensor 462 could include an analyte-sensitive substance that has an optical property that is related to the presence, concentration, or some other property of the analyte. In such examples, the light emitter and/or a light detector could be disposed at a proximal end of the optical fiber, such that the light emitter and light detector illuminate and receive light from the analyte-sensitive substance via the optical fiber of the sensor interconnects 451. Other configurations of the sensor interconnects 451 are anticipated (e.g., capillary tubes, microfluidic elements, etc.).

The sensing platform 400 can be configured to operate using a very low amount of power, e.g., to allow the device to operate to measure a physiological property and to record, indicate, and/or transmit information about the measured physiological property over a protracted period of time, e.g., many hours, days, or weeks. This could include operating the sensing platform 400, during a first period of time, to generate a plurality of digital codes (e.g., using an analog-to-digital converter (ADC) of the sensor interface 452) related to values of the physiological property of interest at respective different points in time (i.e., the generated codes represent samples of the physiological property over time) and to record the generated codes (e.g., in the memory 454). The sensing platform 400 could then operate, during a second period of time, to determine values of the physiological property over time based on the recorded digital codes and calibration data obtained by (e.g., manually input into using the input component 410, received wirelessly using the antenna 470, programmed into during manufacture, determined by a controller of) the sensing platform 400. This conversion could be performed in response to a request (e.g., received from a user via the input component 410, received from an external system via the antenna 470), in response to accessing a power source (e.g., radio frequency energy received wirelessly using the antenna 470 and/or some other element(s) of the power supply 440), or according to some other factors or methods.

Such operation to determine values of a physiological property based on digital codes could require more power and/or energy than the operation of the sensing platform 400 during the first period of time (e.g., to generate and record digital codes relating to the property of interest). Such operation could be performed in response to a request received by the sensing platform 400. For example, a user could operate the input component 410 (e.g., a touch sensor, a button, a capacitive touchscreen) to request an indication of the value of the physiological property, and in response the sensing platform 400 could determine a value of the physiological property based on the most recently generated and recorded digital code and the calibration data. The sensing platform 400 could further provide an indication related to the determined value (e.g., could present a numerical and/or trend indication of the determined value using the display 400). In another example, the sensing platform 400 could receive a request (e.g., by receiving information wirelessly using the antenna 470) for values of the physiological property from the external system 480 and could responsively determine one or more values of the physiological property based on corresponding one or more recorded digital codes and the calibration data. The sensing platform 400 could further transmit the determined values to the external system (e.g., wirelessly, using the antenna 470). Additionally or alternatively, the sensing platform 400 could transmit one or more of the recorded digital codes without converting them into determined values of the physiological property. In some examples, the sensing platform 400 could determine one or more values of the physiological property in response to receiving sufficient radio frequency energy (e.g., using a loop antenna or otherwise configured antenna) to do so.

It is noted that the block diagram shown in FIG. 4 is described in connection with functional modules for convenience in description. However, embodiments of the sensing platform 400 can be arranged with one or more of the functional modules ("sub-systems") implemented in a single chip, integrated circuit, and/or physical feature or on multiple such elements. Further, the sensing platform 400 could be configured to operate without an external system (e.g., reader 480). For example, the sensing platform 400 could lack the antenna 470 and/or communication circuit 456. Further, the power supply 440 could be configured to provide power without receiving such power wirelessly from a reader device, e.g., the power supply 440 could include a battery, could be configured to receive optical and/or radio frequency energy from the environment of the sensing platform 400, or to receive and/or generate power through some other means.

The external reader 480 includes an antenna 488 (or group of more than one antenna) to send and receive wireless signals 471 to and from the sensing platform 400. The external reader 480 also includes a computing system with a processor 486 in communication with a memory 482. The external reader 480 can also include one or more of user controls 485, a display 487, and a communication interface 489. The memory 482 is a non-transitory computer-readable medium that can include, without limitation, magnetic disks, optical disks, organic memory, and/or any other volatile (e.g. RAM) or non-volatile (e.g. ROM) storage system readable by the processor 486. The memory 482 can include a data storage 483 to store indications of data, such as sensor readings (e.g., acquired using the sensors 455, 462), program settings (e.g., to adjust behavior of the sensing platform 400 and/or external reader 480), etc. The memory 482 can also include program instructions 484 for execution by the processor 486 to cause the external reader 480 to perform processes specified by the instructions 484. For example, the program instructions 484 can cause external reader 480 to perform any of the function described herein. For example, program instructions 484 may cause the external reader 480 to provide a user interface that allows for retrieving information communicated from the sensing platform 400 (e.g., sensor outputs from the sensor 462) by displaying that information on the display 487 in response to commands input through the user controls 485. The external reader 480 can also include one or more hardware components for operating the antenna 488 to send and receive the wireless signals 471 to and from the sensing platform 400. For example, oscillators, frequency injectors, encoders, decoders, amplifiers, filters, etc. can drive the antenna 488 according to instructions from the processor 486.

The external reader 480 can also be configured to include a communication interface 489 to communicate signals via a communication medium 491 to and from a remote system 490. For example, the remote system 490 may be a smart phone, tablet computer, laptop computer, or personal computer, and communication interface 489 and communication medium 491 may be a Bluetooth module and wireless Bluetooth communication signals, respectively. In this example, the external reader 480 may be configured to send information about measured physiological properties collected using the sensor(s) 455, 462 to the smart phone, tablet computer, laptop computer, or personal computer for storage and offline analysis. In another example, the remote system 490 is a server at a clinic or physician's office, the communication interface 489 is a WiFi radio module, and the communication medium 491 corresponds to a data network (e.g., the Internet) that enables the transfer of data between the remote server and the WiFi radio module. A physician may use this data to make determinations or diagnoses related to the subject's condition. Further, the external reader 480 may be configured to receive signals from a remote server, such as instructions sent by a physician at a remote location to, for example, increase or decrease sampling frequency. Communication interface 489 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 480 can be a smart phone, digital assistant, or other portable computing device with wireless connectivity sufficient to provide the wireless communication link 471. The external reader 480 can also be implemented as an antenna module that can be plugged in to a portable computing device, such as in an example where the communication link 471 operates at carrier frequencies not commonly employed in portable computing devices. In some instances, the external reader 480 is a special-purpose device configured to be periodically placed relatively near the sensing platform 400 to allow the wireless communication link 471 to operate with a low power budget.

In some examples, the sensor 462 could be configured to detect glucose in the body of a person and the external reader 480 could include or be in contact with an insulin pump. Such an insulin pump could include a supply of insulin and a pump configured to provide the insulin, at a controlled rate, into the body of the person (e.g., through a tube placed in and/or through the skin of the body of the person using, e.g., a needle). In such examples, the insulin pump could be operated based on measurements of glucose levels (e.g., concentrations) in the body of the person detected using the sensor 462. For example, the insulin pump could be operated to provide insulin at a rate based on the detected glucose levels such that the blood glucose levels of the person are maintained within a specified range, or according to some other scheme (e.g., the insulin pump could be operated as part of a feedback loop that includes the sensor 462). Additionally or alternatively, the external reader 480 could include or be in contact with a pump for some other pharmaceutical and could be operated to provide that pharmaceutical at a controlled rate based on a detected level of glucose or of some other analyte or physiological property detected using the sensor 462.

In an example where the sensing platform 400 has been mounted to skin of a living body such that the sensor 462 is in contact with interstitial fluid of the living body, the sensing platform 400 can be operated to detect an analyte (e.g., to measure a concentration of the analyte) in the interstitial fluid. Interstitial fluid is an extravascular fluid that suffuses many of the tissues of a living animal body. The interstitial fluid is continuously replenished by the blood supply through capillaries in the structure of tissue (e.g., dermal tissue, subcutaneous tissue) and includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels in comparison to blood sampling techniques performed by lancing a volume of blood to be analyzed outside a person's body. Moreover, the sensor platform disclosed here can be operated substantially continuously to enable real time measurement of analyte concentrations or other information about an analyte.

In some embodiments, the sensing platform 400 can operate to non-continuously ("intermittently") indicate information related to a physiological property (e.g., concentration values of an analyte in interstitial or other fluids). For example, the sensing platform 400 could operate to periodically operate the sensor 462 to detect an analyte and to store information related to the detection of the analyte in the memory 454. The sensing platform 400 could then less frequently operate to transmit stored information relating to more than one detection of the analyte or other physiological property. Additionally or alternatively, a user could operate the external reader 480 to request such information transmission by the sensing platform 400. In another example, the sensing platform 400 could provide an indication to a user (e.g., via a light, vibration motor, display 420, or other user interface element(s)) that the user should operate the external reader 480 to receive such transmitted information from the sensing platform (e.g., due to the memory 454 being nearly full, due to a battery of the power supply 440 being nearly depleted). Other operations of the systems shown to continuously, periodically, and/or intermittently use the sensor 462 to detect physiological properties, use the memory 454 to store information related to the detected physiological properties, to use the display 420 or other output components to indicate such information, and/or use the antenna 470 to wirelessly indicate such information are anticipated.

IV. EXAMPLE FABRICATION OF A BODY-MOUNTABLE DEVICE

A body-mountable device as described herein (e.g., flexible device that include a display that can be used to provide indications of information, e.g., information about an analyte or other physiological property detected by a sensor of the body-mountable device) can be fabricated in a variety of ways. In some examples, processes used to shape, fabricate, adhere, electrically connect, weld, solder, machine, etch, or otherwise form or fabricate certain elements of such devices could be incompatible in some way with other elements of such devices. For example, electrically connecting electronics to traces disposed on a flexible substrate could require high temperatures (e.g., temperatures sufficient to cause reflow of a metallic solder and/or a flux). Such temperatures could be high enough to cause damage to elements of a display of the device, e.g., to burn and/or oxidize a carrier fluid and/or charged pigment particles of a display medium of the device, to melt a binding agent of such a display medium, and/or to melt a flexible polymer layer of such a display medium. In such examples, the body-mountable device could be fabricated by fabricating a number of layers that could subsequently be adhered or otherwise attached to form the body-mountable sensing device. Further, fabricating a body-mountable sensing device as a number of substantially planar layers could allow such fabrication to be efficiently performed in whole or in part using roll-to-roll processes, such that a plurality of such devices could be formed quickly and cheaply.

As an illustrative example, FIGS. 5A-E show, in cross-section, elements of a body-mountable device as the device is fabricated. The illustrated process of fabrication of a body-mountable device, and any steps or methods described in connection with the execution of such a process, are intended as illustrative examples of the fabrication of a body-mountable device and are not intended to be limiting.

FIG. 5A shows, in cross-section, a flexible substrate 510. On the flexible substrate are disposed first 520a and second 520b layers of metal. These elements could be formed by deposition of the metal layer(s) 520a/b on the flexible substrate (e.g., by chemical vapor deposition, sputtering, physical vapor deposition), deposition of an adhesive layer on the flexible substrate and subsequent deposition of metal foils on such adhesive layers, or some other sequence of steps using one or more processes. Such processes could include spray coating, spin coating, chemical vapor deposition, physical vapor deposition, curing (e.g., thermal curing, ultraviolet curing), or some other deposition process. In some examples, one or more of the layers (e.g., 510, 520a,

520*b*) could be provided as sheets and the one or more layers could be pressed together or otherwise formed (e.g., using an adhesive) into the structure shown in FIG. 5A. For example, the metal layers 520*a*, 520*b* and flexible substrate 510 could be provided as sheets of material (e.g., metal foils and a sheet of polyimide, polyethylene terephthalate, or some other polymer, rubber, or other flexible material) to which an adhesive could be applied (e.g., by spraying, by dipping, by spin-coating) such that the metal layers 520*a*, 520*b* and flexible substrate 510 could be adhered together as shown in FIG. 5A. In some examples, such adhesive layers could be formed from a layer of pressure-sensitive adhesive (e.g., the adhesive layer could be formed from a sheet of a silicone that includes tackifying elements or that has otherwise been configured to be pressure-sensitive) and the structure shown in FIG. 5A could be formed by pressing a metal foil and the flexible substrate 510 against opposite sides of such an adhesive layer.

FIG. 5B shows, in cross-section, the flexible substrate 510 of FIG. 5A after the metal layers 520*a*, 520*b* have been formed into metal traces 535*a*, 535*b*. The formed metal traces 535*a*, 535*b* are configured (e.g., have a shape, size, thickness, composition, conductivity) to provide electrical connections between one or more electronic components. Further, metal traces disposed on the top of the flexible substrate 510 can be formed to form electrodes of a display, e.g., electrodes corresponding to segments of a multi-segment numerical, trend-indicating, or otherwise configured display. The metal layers 520*a*, 520*b* could be formed into the metal traces 535*a*, 535*b* by a variety of methods. In some examples, a photoresist could be applied and patterned using light to expose regions of the metal layers 520*a*, 520*b* that could be subsequently removed (e.g., by a chemical etch process) to leave behind unexposed regions of the metal layers 520*a*, 520*b* that form the metal traces 535*a*, 535*b*. In some examples, a laser, ion beams, engraver, or other means could be used to remove regions of the metal layers 520*a*, 520*b* to form the metal traces 535*a*, 535*b*. Further, forming the metal traces 535*a*, 535*b* from the layers of metal 520*a*, 520*b* could include forming antennas, electrochemical and/or electrophysiological electrodes, electrical contact pads, capacitive touch sensor electrodes, or other shapes or structures.

FIG. 5C shows, in cross-section, the flexible substrate 510 and metal traces 535*a*, 535*b* of FIG. 5B after electronics 540 (e.g., one or more sensors, integrated circuit chips, light emitting diodes, photodiodes, capacitors, resistors) have been disposed on the metal traces 535*a*, 535*b*. The electronics 540 could be disposed on the metal traces 535*a*, 535*b* by pick-and-place machines, by self-assembly, or by some other method. Disposing the electronics 540 on the metal traces 535*a*, 535*b* could include electrically connecting attaching the electronics 540 to the metal traces 535*a*, 535*b*, e.g., by soldering, by applying pressure between the metal traces 535*a*, 535*b* and the electronics 540 by wire-bonding, by use of a conductive material (e.g., a conductive liquid crystal, a conductive epoxy), by reflowing the metal traces 535*a*, 535*b*, or by some other means.

FIG. 5D shows, in cross-section, the flexible substrate 510, metal traces 535*a*, 535*b*, and electronics 550 of FIG. 5C removably mounted in a jig 550 formed to match the shape of the flexible substrate 510 and elements disposed thereon such that a top surface of the flexible substrate 510 (e.g., a surface on which the metal traces 535*b* are disposed) is maintained substantially flat. That is, such a jig could be formed to have a shape corresponding to the shape of a bottom surface of the flexible substrate 510 and elements disposed thereon (e.g., a shape that includes one or more depressions corresponding to the size, shape, and location of integrated circuits, photodiodes, light emitters, resistors, capacitors, or other electronics 540 disposed on the flexible substrate 510).

FIG. 5E shows, in cross-section, the flexible substrate 510, metal traces 535*a*, 535*b*, and electronics 540 of FIG. 5D removably mounted in the jig 550. A display layer 560 has been adhered to the metal traces 535*b*, e.g., by a pressure-sensitive, thermoplastic, or other adhesive. The display layer 560 includes a layer of a display medium (e.g., including a liquid crystal, organic light-emitting diode material, charged pigment particles, or other elements of a display) having a brightness, color, reflectivity, level of light emission, or some other optical property that is electrically controllable (e.g., by applying a specified electric field, voltage, charge and/or current to one or more regions of the display medium) to provide an indication of some information (e.g., to provide multi-segment numerical indication of one or more digits of a detected value of an analyte concentration). The display layer 560 additionally includes a transparent conductive layer disposed opposite the display medium from the metal traces 535*b* such that a voltage and/or current can be applied across and/or through regions of the display medium (e.g., regions corresponding to segments of a multi-segment display) by applying such voltages and/or currents across and/or through the transparent conductive layer and an electrode of the metal traces 535*b* corresponding to the regions of the display medium (e.g., regions corresponding to the segments of the multi-segment display).

FIG. 5F shows, in cross-section, the flexible substrate 510, metal traces 535*a*, 535*b*, electronics 540, and display layer 560 of FIG. 5E removed from the jig 550. Further processing steps could be performed on the device fabricated as illustrated in FIGS. 5A-F. For example, one or more sealant layers could be disposed and/or formed on the device. In some examples, this could include adhering one or more sealant layers (e.g., sealant layers each including one or more of an aluminum foil, a layer of Aclar® barrier film or other substantially moisture-impermeable polymer material, a layer of ultraviolet-stabilized polyethylene terephthalate, one or more layers of pressure-sensitive or otherwise configured adhesive to adhere such elements together to form a sealant layer) to one or both sides of the device (e.g., using a pressure-sensitive or otherwise configured adhesive to adhere such sealant layers to one or both sides of the device). Additionally or alternatively, a conformal sealant layer could be formed around the device and/or additional elements formed and/or disposed thereon (e.g., sealant layers). Such a conformal sealant layer could be formed to adhere to and to at least partially encapsulate the display layer 560, metal traces 535*a*, 535*b*, the electronics 540, and/or elements disposed and/or formed thereon (e.g., sealant layers adhered thereto), e.g., by conformally coating and adhering to exposed surfaces of the device. This could include the conformal sealant layer conformally coating and adhering to surfaces of the metal traces 535*a*, 535*b*, the electronics 540, and/or other elements of the device such that substantially no voids or volumes exist proximate to exposed surfaces of device in which water vapor or other material (e.g., material that has permeated through the conformal sealant layer from a fluid to which the conformal sealant layer is exposed) could be deposited, condense, or otherwise accumulate. The conformal sealant layer could be formed to have a specified thickness, e.g., the conformal sealant layer could have a thickness between approximately 5 microns and approximately 200 microns.

Forming such a conformal sealant layer could include depositing a precursor material (e.g., a solution, vapor, or other material including monomers or other chemicals from which a silicone, rubber, or other material of the conformal sealant layer could be formed) onto device. Depositing the precursor material could include spraying the precursor material, dipping the flexible substrate 510 and elements attached thereto into the precursor material, applying the precursor material via chemical vapor deposition or physical vapor deposition, or applying the precursor material via some other process. Forming the conformal sealant layer could additionally include curing such a deposited precursor material, e.g., by exposing the precursor material to a controlled temperature, by exposing the precursor material to a controlled humidity, by exposing the precursor material to ultraviolet radiation, by exposing the precursor material to a curing agent (e.g., a polymerization initiator), or by some other means. Additionally or alternatively, the conformal sealant layer could be formed by molding (e.g., injection molding). That is, the device could be disposed within a mold, and the conformal sealant layer could be formed by injecting a precursor or other material into the mold to form the conformal sealant layer on the device. Forming the conformal sealant layer could include further steps. In some examples, forming the conformal sealant layer could include exposing the flexible substrate 510 and components disposed thereon to an agent configured to increase the adhesion of the conformal sealant layer to such components (e.g., by exposure to an adhesive material, by exposure to a cleaning solution or cleaning plasma).

A process to fabricate a body-mountable device as described in relation to FIGS. 5A-F could include additional steps. For example, such a process could include controlling a shape of the body-mountable device by cutting the flexible substrate 510 and/or other elements of the device into a specified shape using a laser, a stamp, or some other means. In some examples, one or more of the body-mountable device components could be formed on a sheet of the flexible substrate 510 and specifying the shape of the body-mountable device could include cutting the body-mountable device from such a sheet of flexible material (e.g., by using a laser, stamp, or other means to cut the flexible substrate into a specified shape). Such a specified shape could be specified according to an application. In some examples, the specified shape could include an elongate portion on which a sensor (e.g., an electrochemical sensor including two or more electrodes) is disposed and that is configured to penetrate skin or other tissue. In some examples, such a specified shape could be a ring, circle, arc, or other shape specified to be at least partially embedded in an ophthalmic lens that is, e.g., configured to be mounted to an eye such that a sensor of the formed body-mountable device could be exposed to tears of the eye and/or such that the formed body-mountable device could perform some functions related to the eye.

In some examples, a plurality of body-mountable devices as described herein could be fabricated from a roll of material, e.g., a roll of a flexible substrate, a roll of a flexible substrate on which one or more metal layers are disposed (e.g., adhered to by an adhesive layer), or a roll of some other material. In such examples, one or more processes for fabricating the plurality of body-mountable devices could be performed by unrolling such a roll of material, performing the one or more processes, and rolling the plurality of partially formed body-mountable devices on the material onto a second roll. Further processing to fabricate the plurality of body-mountable devices could include unrolling the second roll of partially formed body-mountable devices on the material and performing one or more further processes on the partially formed body-mountable devices.

V. EXAMPLE METHODS

Figure 6:
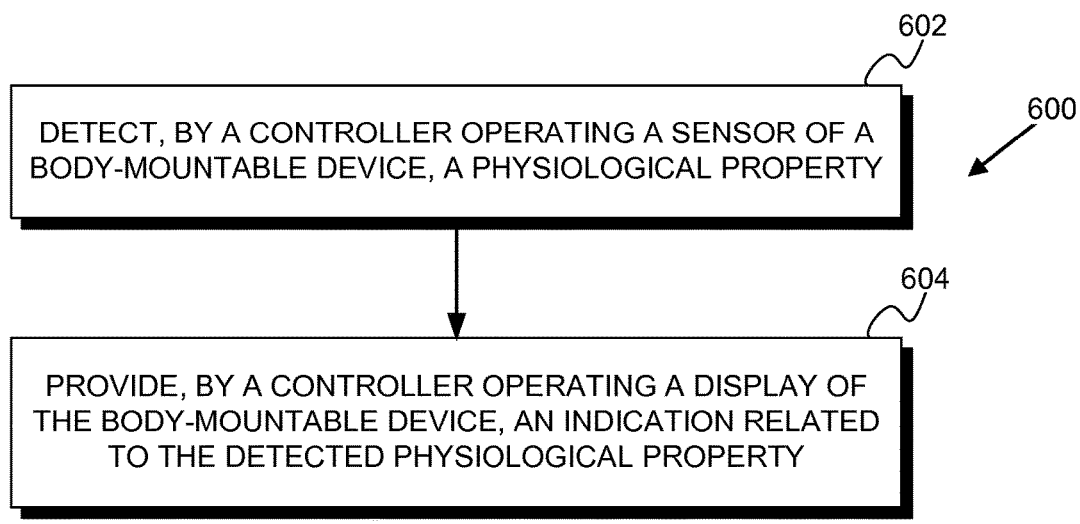
FIG. 6 is a flowchart of an example method.

FIG. 6 is a flowchart of a method 600 for operating a body-mountable device that is mounted to a skin surface. The body-mountable device includes (i) a flexible substrate that is configured to be mounted to the skin surface, (ii) a display disposed on the flexible substrate, wherein the display includes a plurality of electrodes disposed on the flexible substrate, a transparent conductive layer, and a display medium disposed between the plurality of electrodes and the transparent conductive layer, (iii) a sensor probe that has a first end attached to the flexible substrate and a second end that is configured to extend beneath the skin surface to contact interstitial fluid, (iv) a sensor disposed at the second end of the sensor probe and configured to detect a physiological property, where the physiological property includes a property of an analyte in the interstitial fluid, and (v) a controller that is disposed on the flexible substrate and that is electrically coupled to the display and the sensor.

The method 600 includes detecting, by the controller operating the sensor, the physiological property (602). In some examples, the sensor could be a potentiometric electrochemical sensor, and operating the sensor (602) could include measuring a voltage between two or more electrodes. In some examples, the sensor could be an amperometric electrochemical sensor, and operating the sensor (602) could include applying a specified voltage between two or more electrodes and measuring a current through one of the two or more electrodes. In some examples, the sensor could be an optical sensor, and operating the sensor (604) could include illuminating and/or detecting light emitted from a substance that is in contact with a fluid and that has one or more optical properties related to the analyte in the fluid.

Detecting the physiological property (602) could include determining a concentration of the analyte in a fluid, determining that the analyte is present in the fluid (e.g., that the concentration of the analyte in the fluid is above some threshold), determining that the concentration of the analyte is within some specified range of concentrations, determining a state of the analyte (e.g., determining a distribution of isoforms and/or conformational states of the analyte in the fluid), or determining some other information about the analyte. Detecting the physiological property (602) could include determining a concentration or other information about the analyte at a plurality of different points in time (e.g., at a specified rate). Detecting the physiological property (602) could include determining a concentration or other information about the analyte based on calibration data stored by, input into, or otherwise accessible by the body-mountable device (e.g., based on calibration data that describes a relationship between a value of a property (e.g., a voltage, a current) measured by the sensor and a corresponding value of a property of the analyte (e.g., a concentration of the analyte). Detecting the physiological property (602) could be performed in response to a request for such data (e.g., by an external system in communication with the body-mountable device, by a user operating a user interface of the device).

The method 600 further includes providing, by the controller operating the display of the body-mountable device, an indication related to the detected physiological property (604). In some examples, the display could be a multi-segment numerical display, and providing an indication (604) could include operating the multi-segment numerical display to provide a numerical indication (e.g., controlling a color or other optical property of one or more segments of the multi-segment numerical display by applying a voltage and/or current to electrode(s) of the display corresponding to the one or more segments). In some examples, the display could be a multi-segment trend-indicating display, and providing an indication (604) could include operating the multi-segment trend-indicating display to provide an indication of a trend in a detected change over time of the physiological property.

The method 600 could include additional steps. For example, the method 600 could include using a memory of the device to store information relating to the physiological property (e.g., detected analyte concentration values). The method 600 could include wirelessly transmitting information relating to the physiological property. The method 600 could include determining a health state, a course of treatment, a dose and/or timing of administration of a drug, or some other information based on detected analyte data. The method 600 could include providing an indication related to detected analyte data, determined dosing and/or timing of administration of a drug. The method 600 could include determining an alert state based on the obtained physiological property data, e.g., determining that a user is experiencing a medical condition, that a detected physiological parameter (e.g., an analyte concentration) is outside of a specified range of values, that a user could seek medical attention, that a user should receive a drug, or an alert corresponding to some other information.

In some examples, the method 600 could include receiving, via an input component of the body-mountable device (e.g., one or more capacitive touch sensors), calibration information about the operation of the sensor. This could include determining, based on the received input, a calibration value of the physiological property (e.g., of a concentration of the analyte in the interstitial fluid). Such a calibration value could be generated, e.g., by another sensing device (e.g., a lancet and handheld glucose meter, in examples wherein the analyte is glucose). Calibration data could then be determined for the sensor based on the calibration value and further based on the data related to the physiological property obtained using the sensor (e.g., an electrochemical potential and/or current measured by an electrochemical sensor). The method 600 could further include obtaining subsequent data related to the physiological property using the sensor (e.g., operating the sensor a further time to generate further information about the physiological property). A physiological property (e.g., a concentration of the analyte in the interstitial fluid) could be determined based on the determined calibration data and further based on the subsequent data related to the physiological property that was obtained using the sensor.

The method 600 could include mounting the body-mountable device to the skin surface. Mounting the body-mountable device to the skin surface could include using an adhesive layer of the body-mountable device to mount the flexible substrate to the skin surface. Additionally or alternatively, a liquid adhesive, tape, strap, dry adhesive, or other means could be used to mount the flexible substrate to the skin surface. Further, mounting the body-mountable device to the skin surface could include installing the sensor probe in the skin such that the sensor probe penetrates the skin and further such that the sensor disposed on the sensor probe is placed in contact with a fluid (e.g., interstitial fluid) within the skin. This could include placing the sensor probe in a puncture, cut, or other incision that has been formed in the skin (e.g., by a needle, a lancet, a scalpel, or by some other means). Alternatively, the sensor probe could be configured to penetrate and/or pierce the skin (e.g., by being sharpened and/or having a sufficiently high rigidity).

Additional and/or alternative steps, or alternative embodiments of the listed steps, are anticipated.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
   a flexible substrate, wherein the flexible substrate is configured to be mounted to a skin surface;
   a multi-segment display disposed on the flexible substrate, wherein the multi-segment display comprises a plurality of electrodes disposed on the flexible substrate, a transparent conductive layer, and a display medium disposed between the plurality of electrodes and the transparent conductive layer, and wherein each electrode in the plurality of electrodes corresponds to a respective segment of the multi-segment display;

a sensor probe, wherein a first end of the sensor probe is attached to the flexible substrate, wherein a second end of the sensor probe is configured to extend beneath the skin surface to contact interstitial fluid;

a sensor configured to detect a physiological property, wherein the sensor is disposed at the second end of the sensor probe, and wherein the physiological property comprises a property of an analyte in the interstitial fluid; and a controller, wherein the controller is disposed on the flexible substrate, wherein the controller is electrically coupled to the display and the sensor, wherein the controller is configured to perform controller operations comprising:

operating the sensor to detect the physiological property; and operating the display to provide an indication related to the detected physiological property.

2. The body-mountable device of claim 1, wherein the sensor comprises an electrochemical sensor.

3. The body-mountable device of claim 1, wherein at least a portion of the multi-segment display is configured as a multi-segment numerical display in which each segment of the multi-segment numerical display corresponds to a respective electrode in the plurality of electrodes.

4. The body-mountable device of claim 1, wherein at least a portion of the multi-segment display is configured as a multi-segment display that is configured to indicate a trend and in which each segment of the multi-segment display corresponds to a respective electrode in the plurality of electrodes, wherein operating the sensor to detect the physiological property comprises operating the sensor to detect the physiological property at two or more different points in time, and wherein the controller operations further comprise:

determining a trend in the physiological property over time based on the detected physiological property at two or more different points in time, wherein operating the display to provide an indication related to the detected physiological property comprises operating the display to indicate the determined trend.

5. The body-mountable device of claim 1, wherein the display further comprises a transparent flexible polymer layer, wherein the transparent flexible polymer layer is disposed on a side of the transparent conductive layer opposite the display medium, and wherein the transparent flexible polymer layer, the transparent conductive layer, and the display medium are attached to the flexible substrate and the electrodes by a layer of adhesive.

6. The body-mountable device of claim 1, wherein the display medium comprises charged pigment particles.

7. The body-mountable device of claim 6, wherein operating the display comprises applying a voltage between the transparent conductive layer and at least one electrode of the plurality of electrodes, wherein the applied voltage is between 4 volts and 10 volts.

8. The body-mountable device of claim 1, further comprising:

a touch sensor, wherein the controller is electrically coupled to the touch sensor, and wherein the controller operations further comprise operating the touch sensor to receive an input.

9. The body-mountable device of claim 1, further comprising an adhesive layer, wherein the adhesive layer is configured to adhere the flexible substrate to the skin surface.

10. The body-mountable device of claim 1, further comprising a flexible sealant layer, wherein the flexible sealant layer encapsulates the display on the flexible substrate.

11. The body-mountable device of claim 10, wherein the flexible sealant layer comprises silicone.

12. The body-mountable device of claim 1, further comprising a moisture-wicking polymer layer, wherein the moisture-wicking polymer layer is configured to be in contact with the skin surface when the flexible substrate is mounted to the skin surface.

13. The body-mountable device of claim 1, further comprising a flexible battery disposed on the flexible substrate, wherein the flexible battery is configured to supply power to the controller.

* * * * *